United States Patent
Moffitt et al.

(10) Patent No.: US 9,504,818 B2
(45) Date of Patent: *Nov. 29, 2016

(54) MULTIPLE TUNABLE CENTRAL CATHODES ON A PADDLE FOR INCREASED MEDIAL-LATERAL AND ROSTRAL-CAUDAL FLEXIBILITY VIA CURRENT STEERING

(75) Inventors: Michael Moffitt, Valencia, CA (US); Dongchul Lee, Valencia, CA (US); Kerry Bradley, Glendale, CA (US); David K. L. Peterson, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1692 days.

This patent is subject to a terminal disclaimer.

(21) Appl. No.: 12/204,170

(22) Filed: Sep. 4, 2008

(65) Prior Publication Data

US 2010/0057165 A1    Mar. 4, 2010

(51) Int. Cl.
*A61N 1/34* (2006.01)
*A61N 1/05* (2006.01)
*A61N 1/36* (2006.01)

(52) U.S. Cl.
CPC ......... *A61N 1/0551* (2013.01); *A61N 1/36071* (2013.01); *A61N 1/0553* (2013.01)

(58) Field of Classification Search
USPC ................................................. 607/115–117
See application file for complete search history.

(56) References Cited

U.S. PATENT DOCUMENTS

| | | | |
|---|---|---|---|
| 5,417,719 A * | 5/1995 | Hull et al. | ............. 607/46 |
| 5,501,703 A | 3/1996 | Holsheimer et al. | |
| 5,643,330 A | 7/1997 | Holsheimer et al. | |
| 6,052,624 A | 4/2000 | Mann | |
| 6,381,496 B1 | 4/2002 | Meadows et al. | |
| 6,393,325 B1 | 5/2002 | Mann et al. | |
| 6,516,227 B1 | 2/2003 | Meadows et al. | |
| 6,587,724 B2 | 7/2003 | Mann | |
| 6,609,032 B1 | 8/2003 | Woods et al. | |

(Continued)

FOREIGN PATENT DOCUMENTS

| | | |
|---|---|---|
| EP | 1244496 | 6/2001 |
| EP | 1303332 | 12/2004 |

(Continued)

OTHER PUBLICATIONS

PCT Annex to Form PCT/ISA/206 Communication Relating to the Results of the Partial International Search for PCT/US2009/055781, Applicant: Boston Scientific Neuromodulation Corporation, Form PCT/ISA/206, dated Mar. 11, 2010 (7 pages).

(Continued)

*Primary Examiner* — Allen Porter, Jr.
(74) *Attorney, Agent, or Firm* — Schwegman Lundberg & Woessner, P.A.

(57) ABSTRACT

A neurostimulation paddle lead, method of neurostimulation, and neurostimulation system are provided. The neurostimulation paddle lead carries a plurality of electrodes comprising at least four columns of electrodes having a spacing between two inner electrode columns less than a spacing between the inner electrode columns and adjacent outer electrode columns. The inner electrode columns may also be longitudinally offset from the outer electrode columns. The methods and neurostimulation systems steer current between the electrodes to modify a medial-lateral electrical field created adjacent spinal cord tissue.

12 Claims, 16 Drawing Sheets

(56) References Cited

U.S. PATENT DOCUMENTS

| | | |
|---|---|---|
| 6,622,048 B1 | 9/2003 | Mann et al. |
| 6,731,986 B2 | 5/2004 | Mann |
| 6,754,539 B1* | 6/2004 | Erickson et al. ............ 607/117 |
| 6,892,280 B2 | 5/2005 | Nakamura |
| 6,895,280 B2 | 5/2005 | Meadows et al. |
| 6,909,917 B2 | 6/2005 | Woods et al. |
| 6,993,384 B2 | 1/2006 | Bradley et al. |
| 7,177,690 B2 | 2/2007 | Woods et al. |
| 7,539,538 B2 | 5/2009 | Parramon et al. |
| 7,742,819 B2 | 6/2010 | Moffitt |
| 2001/0034542 A1 | 10/2001 | Mann |
| 2002/0022873 A1 | 2/2002 | Erickson et al. |
| 2002/0111661 A1 | 8/2002 | Cross et al. |
| 2003/0114899 A1 | 6/2003 | Woods et al. |
| 2003/0120323 A1 | 6/2003 | Meadows et al. |
| 2003/0139781 A1 | 7/2003 | Bradley et al. |
| 2003/0195582 A1 | 10/2003 | Mann |
| 2004/0034394 A1 | 2/2004 | Woods et al. |
| 2005/0070982 A1 | 3/2005 | Heruth et al. |
| 2005/0107841 A1 | 5/2005 | Meadows et al. |
| 2005/0131506 A1* | 6/2005 | Rezai et al. ................. 607/117 |
| 2005/0143781 A1 | 6/2005 | Carbunaru et al. |
| 2005/0267546 A1 | 12/2005 | Parramon et al. |
| 2006/0106441 A1* | 5/2006 | Ayal et al. .................... 607/118 |
| 2006/0122678 A1 | 6/2006 | Olsen et al. |
| 2006/0253182 A1 | 11/2006 | King |
| 2007/0038250 A1 | 2/2007 | He et al. |
| 2007/0150036 A1 | 6/2007 | Anderson |
| 2007/0168008 A1 | 7/2007 | Olsen |
| 2007/0179579 A1 | 8/2007 | Feler et al. |
| 2007/0276450 A1 | 11/2007 | Meadows et al. |
| 2007/0293914 A1 | 12/2007 | Woods et al. |
| 2008/0109048 A1 | 5/2008 | Moffitt |
| 2008/0140151 A1 | 6/2008 | Brodkey |
| 2008/0215119 A1 | 9/2008 | Woods et al. |
| 2008/0221637 A1 | 9/2008 | Woods et al. |
| 2010/0057163 A1 | 3/2010 | Moffitt et al. |
| 2010/0057164 A1 | 3/2010 | Moffitt et al. |
| 2010/0057165 A1 | 3/2010 | Moffiett et al. |
| 2010/0057177 A1 | 3/2010 | Moffitt et al. |

FOREIGN PATENT DOCUMENTS

| | | |
|---|---|---|
| EP | 1518584 | 3/2005 |
| WO | WO 01/39831 | 6/2001 |
| WO | WO 01/43818 | 6/2001 |
| WO | WO 02/09808 | 2/2002 |
| WO | WO 2005/032654 | 4/2005 |
| WO | WO 2007/087626 | 8/2007 |
| WO | WO 2007/087626 A2 | 8/2007 |
| WO | WO 2007/101999 A2 | 9/2007 |
| WO | WO 2008/005142 A1 | 1/2008 |

OTHER PUBLICATIONS

PCT International Search Report for PCT/US2009/055781, Applicant: Boston Scientific Neuromodulation Corporation, Form PCT/ISA/210 and 220, dated Jun. 9, 2010 (10 pages).

PCT Written Opinion of the International Search Authority for PCT/US2009/055781, Applicant: Boston Scientific Neuromodulation Corporation, Form PCT/ISA/237, dated Jun. 9, 2010 (10 pages).

File History of U.S. Appl. No. 12/204,094, filed Sep. 4, 2008, Inventor: Michael Moffitt et al., entitled: Multiple Tunable Central Cathodes on a Paddle for Increased Medial-Lateral and Rostral-Caudal Flexibiliy Via Current Steering.

Notice of Allowance dated Nov. 8, 2010, in U.S. Appl. No. 12/204,094, filed Sep. 4, 2008, Inventor: Michael Moffitt et al., (14 pages).

Non-Final Office Action dated Jun. 9, 2010, in U.S. Appl. No. 12/204,094, filed Sep. 4, 2008, Inventor: Michael Moffitt et al., (18 pages).

File History of U.S. Appl. No. 12/204,114, filed Sep. 4, 2008, Inventor: Michael Moffitt et al., entitled: Multple Tunable Central Cathodes on a Paddle for Increased Medial-Lateral and Rostral-Caudal Flexibility Via Current Steering.

Final Office Action dated Jan. 21, 2011 in U.S. Appl. No. 12/204,114, filed Sep. 4, 2008, Inventor: Michael Moffitt (9 pages).

Non-Final Office Action dated Sep. 28, 2010 in U.S. Appl. No. 12/204,114, filed Sep. 4, 2008, Inventor: Michael Moffitt, (18 pages).

File History of U.S. Appl. No. 12/204,136, filed Sep. 4, 2008; Inventor: Michael Moffitt et al., Entitled: Multiple Tunable Central Cathodes on a Paddle for Increased Medial-Lateral and Rostral-Caudal Flexibility Via Current Steering.

Non-Final Office Action dated Nov. 5, 2010, in U.S. Appl. No. 12/204,136, Inventor: Michael Moffitt, (18 pages).

File History of U.S. Appl. No. 12/204,154, filed Sep. 4, 2008; Inventor: Michael Moffitt et al., Entitled: Multiple Tunable Central Cathodes on a Paddle for Increased Medial-Lateral and Rostral-Caudal Flexibility Via Current Steering.

Appeal Brief dated Feb. 25, 2011 in U.S. Appl. No. 12/204,154, filed Sep. 4, 2008; inventor: Michael Moffitt, (17 pages).

Advisory Action dated Jan. 21, 2011 in U.S. Appl. No. 12/204,154, filed Sep. 4, 2008; inventor: Michael Moffitt, (4 pages).

Final Office Action dated Nov. 8, 2010 in U.S. Appl. No. 12/204,154, filed Sep. 4, 2008; inventor: Michael Moffit (9 pages).

Non-Final Office Action dated Jun. 17, 2010 in U.S. Appl. No. 12/204,154, filed Sep. 4, 2008; inventor: Michael Moffitt, (19 pages).

PCT International Preliminary Report on Patentability (Chapter I of the Patent Cooperation Treaty) for PCT/US2009/055781, Applicant: Boston Scientific Neuromodulation Corporation, Form PCT/IB/326 and 373, dated Mar. 17, 2011 (12pages).

Notice of Allowance dated Mar. 22, 2011 in U.S. Appl. No. 12/204,094, filed Sep. 4, 2008, Inventor: Michael Moffitt et al. (15 pages).

Final Office Action dated Mar. 23, 2011 in U.S. Appl. No. 12/204,136, filed Sep. 4, 2008, Inventor: Michael Moffitt et al., (9 pages).

Advisory Action dated Apr. 14, 2011 in U.S. Appl. No. 12/204,136, filed Sep. 4, 2008, Inventor: Michael Moffitt et al., (3 pages).

Advisory Action dated May 5, 2011 in U.S. Appl. No. 12/204,136, inventor: Michael Moffitt et al., (2 pages).

Appeal Brief dated May 16, 2011 in U.S. Appl. No. 12/204,136, inventor: Michael Moffitt et al., (16 pages).

Examiner's Answer dated Apr. 22, 2011 in U.S. Appl. No. 12/204,154, inventor: Michael Moffitt et al., (8 pages).

Reply Brief dated May 16, 2011 in U.S. Appl. No. 12/204,054, inventor: Michael Moffitt et al., (4 pages).

Non-Final Office Action dated Jun. 22, 2011 in U.S. Appl. No. 12/204,114, inventor: Michael Moffitt et al., (13 pages).

Examiner's Answer dated Aug. 2, 2011 in U.S. Appl. No. 12/204,136, inventor: Michael Moffitt et al, (9pages).

Reply Brief dated Sep. 14, 2011 in U.S. Appl. No. 12/204,136, inventor: Michael Moffitt et al., (4pages).

* cited by examiner

MULTIPLE TUNABLE CENTRAL CATHODES ON A PADDLE FOR INCREASED MEDIAL-LATERAL AND ROSTRAL-CAUDAL FLEXIBILITY VIA CURRENT STEERING

RELATED APPLICATIONS

This application is filed concurrently with U.S. patent application Ser. Nos. 12/204,094, 12/204,114, 12/204,136, 12/204,154, the disclosure of which are expressly incorporated herein by reference.

FIELD OF THE INVENTION

The present invention relates to tissue stimulation systems, and more particularly, to systems and methods for electrically stimulating spinal cord tissue.

BACKGROUND OF THE INVENTION

Spinal cord stimulation (SCS) is a well-accepted clinical method for reducing pain in certain populations of patients. During SCS, the spinal cord, spinal nerve roots, or other nerve bundles are electrically stimulated using one or more neurostimulation leads implanted adjacent the spinal cord. While the pain-reducing effect of SCS is not well understood, it has been observed that the application of electrical energy to particular regions of the spinal cord induces paresthesia (i.e., a subjective sensation of numbness or tingling) that replaces the pain signals sensed by the patient in the afflicted body regions associated with the stimulated spinal regions. Thus, the paresthesia appears to mask the transmission of chronic pain sensations from the afflicted body regions to the brain.

In a typical procedure, one or more stimulation leads are introduced through the patient's back into the epidural space under fluoroscopy, such that the electrodes carried by the leads are arranged in a desired pattern and spacing to create an electrode array. The specific procedure used to implant the stimulation leads will ultimately depend on the type of stimulation leads used. Currently, there are two types of commercially available stimulation leads: a percutaneous lead and a surgical lead.

A percutaneous lead comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline. A surgical lead has a paddle on which multiple electrodes are arranged typically in independent columns, and is introduced into contact with the affected spinal tissue using a surgical procedure, and specifically, a laminectomy, which involves removal of the laminar vertebral tissue to allow both access to the dura layer and positioning of the lead.

Stimulation energy may be delivered to the electrodes of the leads during and after the placement process in order to verify that the leads are stimulating the target neural tissue. Stimulation energy is also delivered to the electrodes at this time to formulate the most effective set of stimulus parameters, which include the electrodes that are sourcing (anodes) or returning (cathodes) the stimulation pulses at any given time, as well as the magnitude and duration of the stimulation pulses. During the foregoing procedure, an external trial neurostimulator may be used to convey the stimulation pulses to the lead(s), while the patient provides verbal feedback regarding the presence of paresthesia over the pain area. The stimulus parameter set will typically be one that provides stimulation energy to all of the target tissue that must be stimulated in order to provide the therapeutic benefit (e.g., pain relief), yet minimizes the volume of non-target tissue that is stimulated, which may correspond to unwanted or uncomfortable paresthesia. Thus, neurostimulation leads are typically implanted with the understanding that the stimulus parameter set will require fewer than all of the electrodes on the leads to achieve the desired paresthesia.

After the lead(s) are placed at the target area of the spinal cord, the lead(s) are anchored in place, and the proximal ends of the lead(s), or alternatively lead extensions, are passed through a tunnel leading to a subcutaneous pocket (typically made in the patient's abdominal area) where a neurostimulator is implanted. The lead(s) are connected to the neurostimulator, which is programmed with the stimulation parameter set(s) previously determined during the initial placement of the lead(s). The neurostimulator may be operated to test the effect of stimulation and, if necessary, adjust the programmed set(s) of stimulation parameters for optimal pain relief based on verbal feedback from the patient. Based on this feedback, the lead position(s) may also be adjusted and re-anchored if necessary. Any incisions are then closed to fully implant the system.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead or leads being placed in a location (both longitudinal and lateral) relative to the spinal tissue such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy.

Even after successful placement of the leads in the operating room (with corresponding test stimulation), the SCS system typically requires electrical fine-tuning post-operatively, and often it is difficult to target all pain areas, with some areas (e.g., the lower back) being particularly difficult to target. In particular, lead migration may relocate the paresthesia away from the pain site, resulting in the target neural tissue no longer being appropriately stimulated and the patient no longer realizing the full intended therapeutic benefit. With electrode programmability, the stimulation area can often be moved back to the effective pain site without having to reoperate on the patient in order to reposition the lead. For example, some SCS systems use changes in electrode polarity or incremental electrical current shifts in the cathodes and anodes to tune the location of paresthesia.

To produce the feeling of paresthesia without inducing discomfort or involuntary motor movements within the patient, it is often desirable to preferentially stimulate nerve fibers in the dorsal column (DC nerve fibers), which primarily include sensory nerve fibers, over nerve fibers in the dorsal roots (DR nerve fibers), which include both sensory nerve fibers and motor reflex nerve fibers. In order to stimulate the DC nerve fibers, while guarding against the stimulation of the DR nerve fibers, SCS systems may activate anodes that flank a single cathode in a medial-lateral electrical field, with the single cathode providing the stimulation energy for the DC fibers, while the flanking anodes guarding against the over-stimulation of the DR fibers, as illustrated in FIG. 1.

While change in the relative anode strengths will yield some tunability with a multiple source system, the electrical field is "tethered" to the single cathode, and so has limited flexibility in medial-lateral tuning. In fact, some hypotheses would suggest that "lower-back fibers" are off-midline, and thus a single cathode located over the center of the spinal cord may not be the optimum position for the cathode.

Also, the fixed spacing between the anodes and the cathode in a 3-column medial-lateral electrode arrangement is limiting, because the spacing would ideally be optimized to the distance from the electrodes to the spinal cord (due, e.g., to cerebral spinal fluid thickness (dCSF)), and that is a parameter with substantial variability between patients and at different vertebral levels within a patient. That is, in the case of a high dCSF, the spinal cord tissue will be relatively far away from the electrodes, and, therefore, it is desirable to increase the spacing between the anodes and cathode to lower the stimulation threshold by reducing the shunting of current, thus preventing excessive amplitudes. In the case of a low dCSF, the spinal cord tissue will be relatively close to the electrodes, and thus, current shunting (i.e., decay of field strength) is not as critical. In this case, it is desirable to increase the tunability of the stimulation by decreasing the spacing between the anodes and cathode. However, because the physical spacing between the anodes and cathode is fixed, and prior art SCS systems do not have the capability of electrically adjusting the spacing between the flanking anodes and the single cathode, variations in the dCSF cannot be suitably accounted for in prior art SCS systems. In addition, in a prior art medial-lateral arrangement, the electrodes are uniformly spaced and rostral-caudally aligned with each, which may not be the optimum arrangement.

There, thus, remains a need for an improved SCS system with improved targeting capability using a medial-lateral electrode arrangement.

SUMMARY OF THE INVENTION

In accordance with a first aspect of the present inventions, a neurostimulation paddle lead comprises at least one elongated lead body, a plurality of terminals carried by the proximal end of the lead body, and a paddle-shaped membrane disposed on the distal end of the lead body(ies). In one embodiment, the paddle-shaped membrane is sized and shaped to be disposed within the epidural space of a patient. The paddle lead further comprises a plurality of electrodes arranged on an exterior surface of the paddle-shaped membrane in electrical communication with the respective terminals.

The plurality of electrodes comprises at least four electrodes extending along the paddle-shaped membrane in a direction transverse to the longitudinal axis of the lead body. These electrodes include first and second inner electrodes immediately adjacent to each other, a first outer electrode immediately adjacent to the first inner electrode, and a second outer electrode immediately adjacent to the second inner electrode. A first transverse spacing between the first and second inner electrodes is different from each of a second transverse spacing between the first inner electrode and the first outer electrode, and a third transverse spacing between the second inner electrode and the second outer electrode. For example, the first transverse spacing can be less than each of the second and third transverse spacings. In one embodiment, the first transverse spacing is within the range of 1.5-4.0 mm, and each of the second and third transverse spacings, which may be equal to each other, is within the range of 1.5-4.0 mm. In another embodiment, the transverse spacing between the first and second outer electrodes is within the range of 4.5-11.0 mm. In another embodiment, the first and second inner electrodes are offset from the first and second outer electrodes along the longitudinal axis.

In accordance with a second aspect of the present inventions, another neurostimulation paddle lead is similar to the previously described paddle lead, with the exception that the plurality of electrodes comprises at least four columns of electrodes. Each electrode column extends along the paddle-shaped membrane in a longitudinal direction, with the electrode columns having first and second inner electrode columns immediately adjacent to each other, a first outer electrode column immediately adjacent to the first inner electrode column, and a second outer electrode column immediately adjacent to the second inner electrode column. The first transverse spacing between the first and second inner electrode columns is different for each of a second transverse spacing between the first inner electrode column and the first outer electrode column, and a third transverse spacing between the second inner electrode column and the second outer electrode column. For example, the first transverse spacing can be less than each of the second and third transverse spacings. In one embodiment, the first transverse spacing is within the range of 1.5-4.0 mm, and each of the second and third transverse spacings, which may be equal to each other, is within the range of 1.5-4.0 mm. In another embodiment, the transverse spacing between the first and second outer electrode columns is within the range of 4.5-11.0 mm. In another embodiment, the first and second inner electrode columns are offset from the first and second outer electrode columns along the longitudinal axis.

In accordance with a third aspect of the present inventions, a method of providing therapy to a patient comprises disposing at least four electrodes adjacent spinal cord tissue of the patient (e.g. in the epidural space of the patient) in a medial-lateral electrode arrangement. The electrodes include first and second inner electrodes immediately adjacent to each other, a first outer electrode immediately adjacent to the first inner electrode, and a second outer electrode immediately adjacent to the second inner electrode. A first medial-lateral spacing between the first and second inner electrodes is different from each of a second medial-lateral spacing between the first inner electrode and the first outer electrode, and a third medial-lateral spacing between the second inner electrode and the second outer electrode. For example, the first medial-lateral spacing can be less than each of the second and third medial-lateral spacings.

In one method, the first medial-lateral spacing is within the range of 1.5-4.0 mm, and each of the second and third medial-lateral spacings, which may be equal to each other, is within the range of 1.5-4.0 mm. In another method, the medial-lateral spacing between the first and second outer electrodes is within the range of 4.5-11.0 mm. In another method, the first and second inner electrodes are rostralcaudally offset from the first and second outer electrodes.

The method further comprises configuring at least one of the first and second inner electrodes as a cathode, and at least one of the first and second outer electrodes as an anode. In one method, the both of the first and second inner electrodes are configured as cathodes, and both of the outer electrodes are configured as anodes. The method further comprises conveying electrical energy between the cathode(s) and the anode(s) that creates a medial-lateral electrical field that stimulates the spinal cord tissue.

In accordance with a fourth aspect of the present invention, a neurostimulation paddle lead comprises at least one elongated lead body, a plurality of terminals carried by the proximal end of the lead body, and a paddle-shaped membrane disposed on the distal end of the lead body(ies). In one embodiment, the paddle-shaped membrane is sized and shaped to be disposed within the epidural space of a patient. The paddle lead further comprises a plurality of electrodes arranged on an exterior surface of the paddle-shaped membrane in electrical communication with the respective terminals.

The plurality of electrodes comprises at least four columns of electrodes, with each column extending along the paddle-shaped membrane in a longitudinal direction. The electrode columns include at least two inner electrode columns and outer electrode columns flanking the inner electrode column(s). At least one of the inner electrode columns is offset from the outer electrode columns in the longitudinal direction. In one embodiment, at least one electrode in each of the inner electrode columns is equi-distant between two immediately adjacent electrodes in each of the outer electrode columns.

In one embodiment, the inner electrode columns comprises first and second immediately adjacent inner electrode columns, a first one of the outer electrode columns is immediately adjacent the first inner electrode column, and a second one of the outer electrode columns is immediately adjacent the second inner electrode column. In this case, a first transverse spacing between the first and second inner electrode columns may be different from each of a second transverse spacing between the first inner electrode column and the first outer electrode column, and a third transverse spacing between the second inner electrode column and the second outer electrode column. For example, the first transverse spacing can be less than each of the second and third transverse spacings. In one embodiment, the first transverse spacing is within the range of 1.5-4.0 mm, and each of the second and third transverse spacings, which may be equal to each other, is within the range of 1.5-4.0 mm. In another embodiment, the transverse spacing between the first and second outer electrode columns is within the range of 4.5-11.0 mm. In another embodiment, the first and second inner electrode columns are offset from the first and second outer electrode columns along the longitudinal axis.

In accordance with a fifth aspect of the present inventions, a method of providing therapy to a patient comprises disposing at least four columns of electrodes adjacent spinal cord tissue of the patient (e.g., within the epidural space of the patient), with the electrode column(s) have at least two inner electrode columns and outer electrode columns flanking the inner electrode column(s).

The method further comprises configuring at least one electrode in the inner electrode column as a cathode, and at least two immediately adjacent electrodes in each of at least one of the outer electrode columns as anodes, with the anodes being positioned both rostrally and caudally relative to the cathode(s). The method further comprises conveying electrical energy between the cathode(s) and the anodes to create a medial-lateral electrical field that stimulates the spinal cord tissue.

In one method, at least one electrode in each of the two inner electrode columns is configured as a cathode. In this case, the cathodes may be immediately adjacent to each other, and electrodes in both the outer electrode columns can be configured as anodes. In another method, at least one electrode in only one of the two inner electrode columns is configured as a cathode. In this case, electrodes in both the outer columns(s) may be configured as anodes, or electrodes in only the outer electrode column immediately adjacent the inner electrode column may be configured as anodes, or electrodes in only the outer electrode column that is not immediately adjacent the inner electrode column may be configured as anodes.

In still another method, electrodes in first and second inner electrode columns that are immediately adjacent to each other are configured as cathodes, and anodes in a first outer electrode column immediately adjacent to the first inner electrode column, and electrodes in a second outer electrode column immediately adjacent to the second inner electrode column are configured as anodes. In this case, a first transverse spacing between the first and second inner electrode columns is different from each of a second transverse spacing between the first inner electrode column and the first outer electrode column, and a third transverse spacing between the second inner electrode column and the second outer electrode column. For example, the first transverse spacing can be less than each of the second and third transverse spacings.

In accordance with a sixth aspect of the present inventions, a method of providing therapy to a patient comprises disposing at least four electrodes adjacent the spinal cord tissue of the patient (e.g., in the epidural space) in a medial-lateral electrode arrangement. The electrodes include two inner electrodes and two outer electrodes flanking the two inner electrodes. The method further comprises configuring the inner electrodes as cathodes, and the outer electrodes as anodes, and conveying electrical energy between the cathodes and the anodes to create a medial-lateral electrical field that stimulates the spinal cord tissue; for example, by stimulating the dorsal column fibers without stimulating the dorsal root fibers.

The method further comprises incrementally shifting cathodic current between the cathodes (e.g., in increments equal to or less than 10 percent) to modify the medial-lateral electrical field. For example, the cathodic current may be incrementally shifted between the cathodes to spatially shift the medial-lateral electrical field transversely relative to dorsal column fibers of the spinal cord tissue. One method further comprises incrementally shifting anodic current between the anodes to modify the medial-lateral electrical field.

In accordance with a seventh aspect of the present inventions, a neurostimulation system for providing therapy to a patient comprises a neurostimulation paddle lead carrying a plurality of electrodes comprising at least four electrodes extending in a direction transverse to a longitudinal axis of the paddle lead. In one embodiment, the paddle lead is sized to be implanted within an epidural space above spinal cord tissue of the patient. The electrodes include two inner electrodes and two outer electrodes flanking the two inner electrodes.

The neurostimulation system further comprises a neurostimulator for configuring the inner electrodes as cathodes and the outer electrodes as anodes, and for conveying electrical energy between the cathodes and the anodes to create an electrical field that stimulates tissue of the patient; for example, by stimulating the dorsal column fibers without stimulating the dorsal root fibers. The neurostimulator is further configured for incrementally shifting cathodic current between the cathodes (e.g., in increments equal to or less than 10 percent) to modify the electrical field. For example, the neurostimulator may be configured for incrementally shifting the cathodic current between the cathodes to spatially shift the electrical field transversely relative to dorsal column fibers of the spinal cord tissue. In one embodiment, the neurostimulator is configured for incrementally shifting anodic current between the anodes to modify the electrical field.

In accordance with an eighth aspect of the present inventions, a method of providing therapy to a patient comprises disposing at least four columns of electrodes adjacent spinal cord tissue of the patient (e.g., within the epidural space). The electrode columns include two inner electrode columns and two outer electrode columns flanking the two inner electrode columns. The method further comprises configuring at least two electrodes of the inner electrode columns as cathodes, and at least one electrode of each of the outer electrode columns as anodes, conveying electrical energy between the cathodes and the anodes to create a medial-lateral electrical field that stimulates the spinal cord tissue (for example, by stimulating the dorsal column fibers without stimulating the dorsal root fibers), and incrementally shifting cathodic current between the cathodes (e.g., in increments equal to or less than 10 percent) to modify the medial-lateral electrical field.

In one method, the cathodes are rostral-caudally aligned relative to each other (i.e., the cathodes are at the same rostral-caudal level), such that incremental shifting of the cathodic current between the cathodes spatially shifts the medial-lateral electrical field transversely relative to dorsal column fibers of the spinal cord tissue. In another method, the cathodes are rostral-caudally offset from each other, such that incremental shifting of the cathodic current between the cathodes rostral-caudally expands the medial-lateral electrical field.

In accordance with a ninth aspect of the present inventions, a neurostimulation system for providing therapy to a patient comprises a neurostimulation paddle lead carrying a plurality of electrodes comprising at least four columns of electrodes extending along a longitudinal axis of the paddle lead. The electrode columns include two inner electrode columns and two outer electrode columns flanking the two inner electrode columns. In one embodiment, the paddle lead is sized to be implanted within an epidural space above spinal cord tissue of the patient.

The neurostimulation system further comprises a neurostimulator for configuring at least two electrodes of the inner electrode columns as cathodes, and at least one electrode of each of the outer electrode columns as anodes, conveying electrical energy between the cathodes and the anodes to create an electrical field that stimulates tissue of the patient (for example, by stimulating the dorsal column fibers without stimulating the dorsal root fibers), and incrementally shifting cathodic current between the cathodes (e.g., in increments equal to or less than 10 percent) to modify the electrical field. In one embodiment, the cathodes are longitudinally aligned relative to each other (i.e., the cathodes are at the same longitudinal level), such that incremental shifting of the cathodic current between the cathodes spatially shifts the electrical field transversely relative to the longitudinal axis. In another embodiment, the cathodes are longitudinally offset from each other, such that incremental shifting of the cathodic current between the cathodes expands the electrical field along the longitudinal axis.

In accordance with a tenth aspect of the present inventions, a method of providing therapy to a patient comprises disposing at least four electrodes adjacent spinal cord tissue of the patient (e.g., in the epidural space) in a medial-lateral electrode arrangement. The electrodes include two inner electrodes and two outer electrodes flanking the two inner electrodes. In one method, the transverse pacing between the second one of the inner electrodes and the first one of the inner electrodes is less than the transverse spacing between a closest one of the outer electrodes and the second one of the inner electrodes.

The method further comprises configuring a first one of the inner electrodes as a cathode, a second one of the inner electrodes as one of a cathode and an anode, and the outer electrodes as anodes, and conveying electrical energy between the cathodes and the anodes to create a medial-lateral electrical field that stimulates the spinal cord tissue; for example, by stimulating the dorsal column fibers without stimulating the dorsal root fibers. The method further comprises reconfiguring the second one of the inner electrodes as the other of the cathode and the anode, and reconveying electrical energy between the cathodes and the anodes to create a medial-lateral electrical field that stimulates the spinal cord tissue.

One method further comprises incrementally shifting (e.g., in increments equal to or less than 10 percent) cathodic current between the cathodes and/or anodic current between the anodes to modify the medial-lateral electrical field. For example, the cathodic current may be incrementally shifted between the cathodes to spatially shift the medial-lateral electrical field transversely relative to dorsal column fibers of the spinal cord tissue.

In accordance with an eleventh aspect of the present inventions, a neurostimulation system for providing therapy to a patient comprises a neurostimulation paddle lead carrying a plurality of electrodes comprising at least four electrodes extending in a direction transverse to a longitudinal axis of the paddle lead. The electrodes include two inner electrodes and two outer electrodes flanking the two inner electrodes. In one embodiment, the paddle lead is sized to be implanted within an epidural space above spinal cord tissue of the patient. In another embodiment, the spacing between the second one of the inner electrodes and the first one of the inner electrodes is less than the spacing between a closest one of the outer electrodes and the second one of the inner electrodes.

The neurostimulation system further comprises a neurostimulator for configuring a first one of the inner electrodes as a cathode, a second one of the inner electrodes as one of a cathode and an anode, and the outer electrodes as anodes, conveying electrical energy between the cathodes and the anodes to create an electrical field that stimulates tissue of the patient (for example, by stimulating the dorsal column fibers without stimulating the dorsal root fibers), reconfiguring the second one of the inner electrodes as the other of the cathode and the anode, and reconveying electrical energy between the cathodes and the anodes to create an electrical field that stimulates the tissue. In one embodiment, the neurostimulator is further configured for incrementally shifting cathodic current between the cathodes and/or anodic current between the anodes (e.g., in increments equal to or less than 10 percent) to modify the electrical field. For example, the cathodic current may be incrementally shifted between the cathodes to spatially shift the medial-lateral electrical field transversely relative to dorsal column fibers of the spinal cord tissue.

In accordance with a twelfth aspect of the present inventions, a method of providing therapy to a patient comprises disposing at least four electrodes adjacent spinal cord tissue of the patient (e.g., in the epidural space) in a medial-lateral electrode arrangement. The electrodes include two inner electrodes and two outer electrodes flanking the two inner electrodes.

The method further comprises conveying electrical energy between the electrodes to create a medial-lateral electrical field having a locus on one lateral side of the midline of the spinal cord tissue (e.g., by configuring only a first one of the inner electrodes as a cathode or configuring a first one of the inner electrodes to have more cathodic current than a second one of the inner electrodes), and conveying electrical energy between the electrodes to create a medial-lateral electrical field having a locus on the other lateral side of the midline of the spinal cord tissue (e.g., by configuring only a second one of the inner electrodes as a cathode or by configuring the second one of the inner electrodes to have more cathodic current than the first one of the inner electrodes). In one method, the medial-lateral electrical fields stimulate the dorsal column fibers without stimulating dorsal root fibers within the spinal cord tissue.

In accordance with a thirteenth aspect of the present invention, a neurostimulation system for providing therapy to a patient comprises a neurostimulation paddle lead configured for being implanted within an epidural space above spinal cord tissue of the patient. The neurostimulation paddle lead carries a plurality of electrodes comprising at least four electrodes extending in a direction transverse to a longitudinal axis of the paddle lead. The electrodes include two inner electrodes and two outer electrodes flanking the two inner electrodes.

The neurostimulator is configured for conveying electrical energy between the electrodes to create a medial-lateral electrical field having a locus on one lateral side of the midline of the spinal cord tissue (e.g., by configuring only a first one of the inner electrodes as a cathode or configuring a first one of the inner electrodes to have more cathodic current than a second one of the inner electrodes), and conveying electrical energy between the electrodes to create a medial-lateral electrical field having a locus on the other lateral side of the midline of the spinal cord tissue (e.g., by configuring only a second one of the inner electrodes as a cathode or by configuring the second one of the inner electrodes to have more cathodic current than the first one of the inner electrodes). In one embodiment, the neurostimulator is configured for conveying the electrical energy between the cathodes and the anodes to create an electrical field that stimulates the dorsal column fibers without stimulating dorsal root fibers within the spinal cord tissue.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
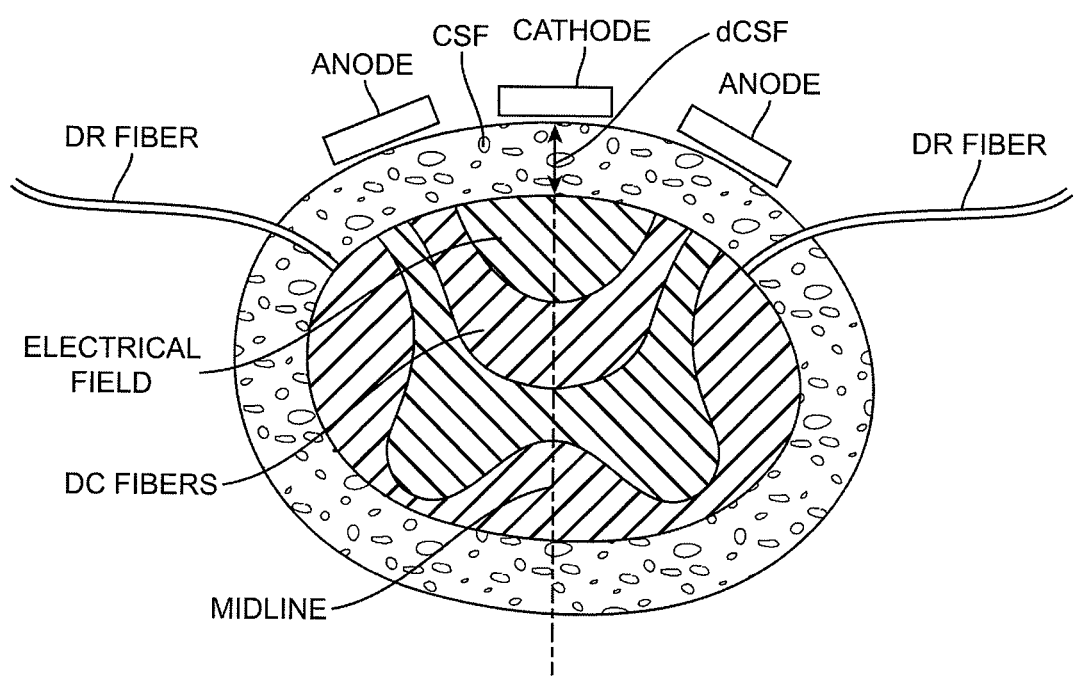
FIG. 1 is a cross-sectional view of a spinal cord and a prior art electrode arrangement for creating a medial-lateral electrical field that stimulates the spinal cord.
Figure 2:
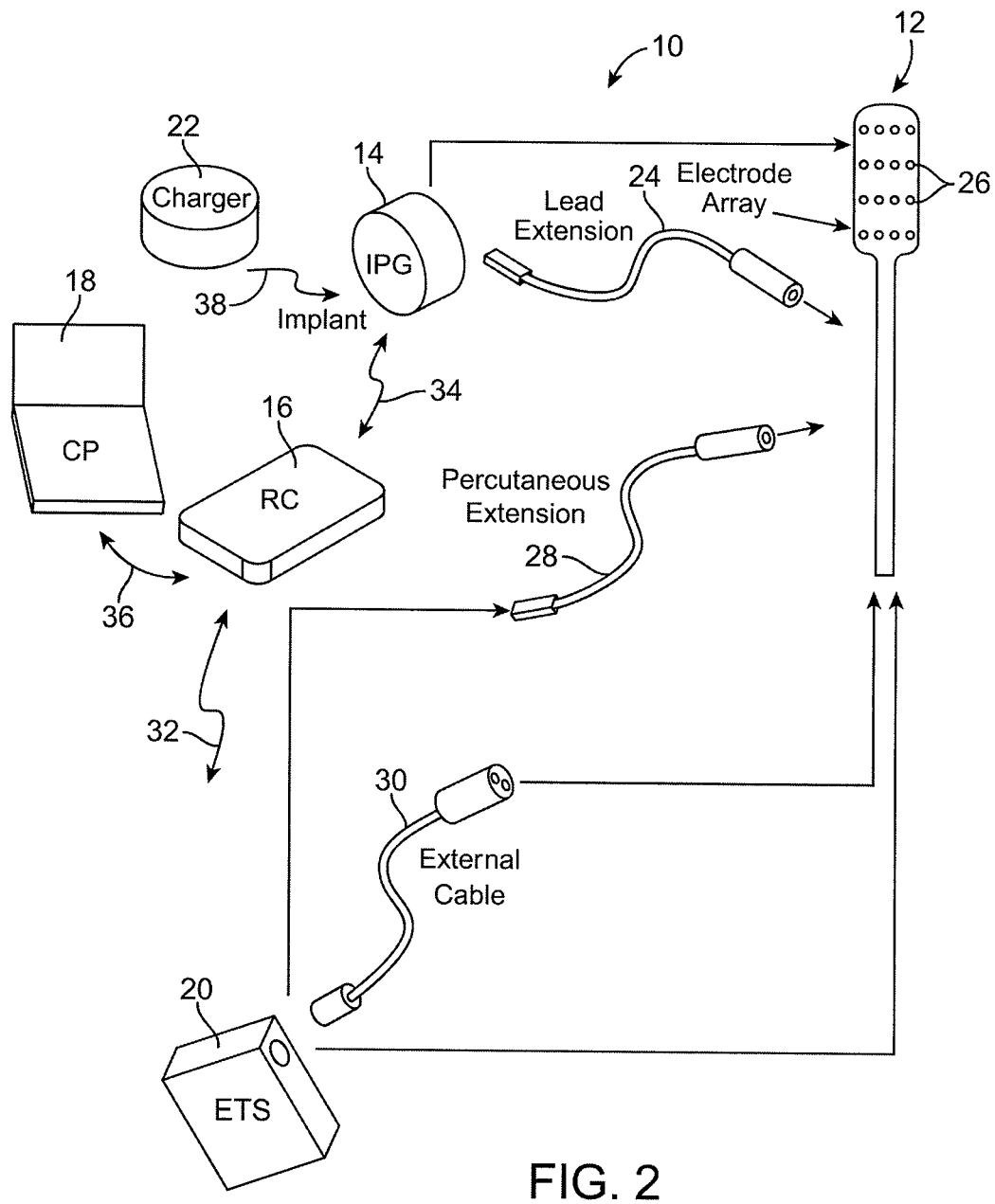
FIG. 2 is plan view of one embodiment of a spinal cord stimulation (SCS) system arranged in accordance with the present inventions.

Turning first to FIG. 2, an exemplary spinal cord stimulation (SCS) system 10 generally comprises an implantable stimulation lead 12, an implantable pulse generator (IPG) 14 (or alternatively RF receiver-stimulator), an external remote control RC 16, a Clinician's Programmer (CP) 18, an External Trial Stimulator (ETS) 20, and an external charger 22.

The IPG 14 is physically connected via a lead extension 24 to the stimulation lead 12, which carries a plurality of electrodes 26 arranged in an array. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20, which has similar pulse generation circuitry as the IPG 14, also provides electrical stimulation energy to the electrode array 26 in accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the effectiveness of the stimulation that is to be provided.

The RC 16 may be used to telemetrically control the ETS 20 via a bi-directional RF communications link 32. Once the IPG 14 and stimulation lead 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The external charger 22 is a portable device used to transcutaneously charge the IPG 14 via an inductive link 38.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 3:
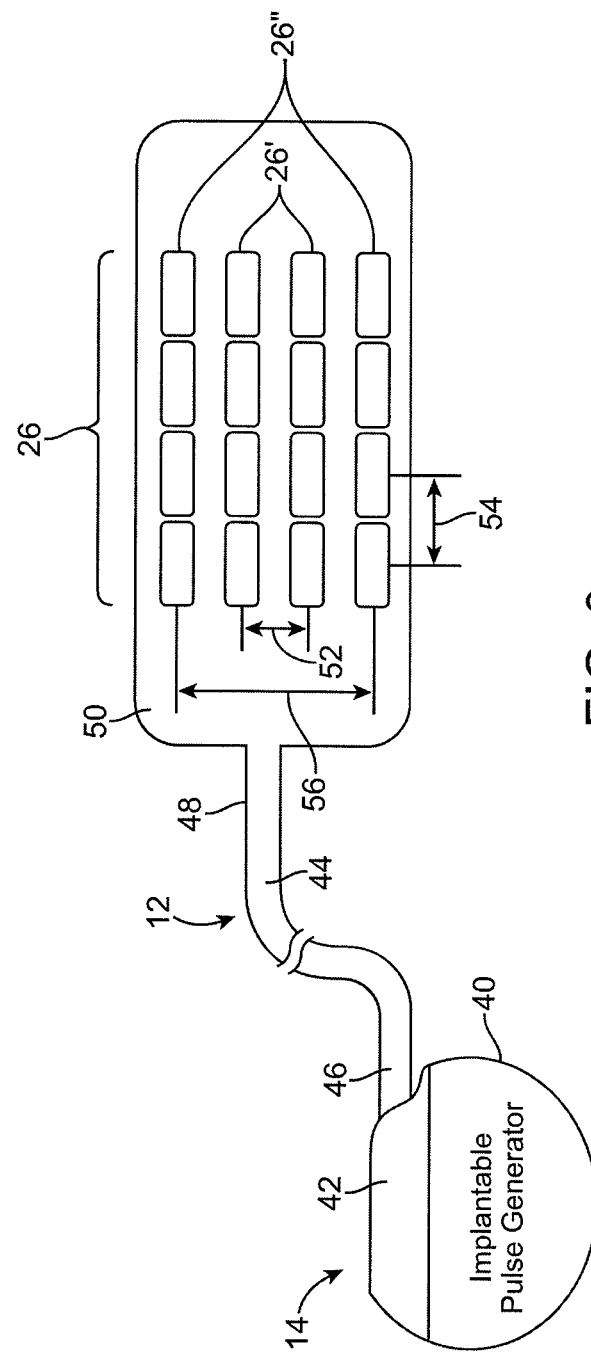
FIG. 3 is a profile view of an implantable pulse generator (IPG) and one embodiment of a neurostimulation paddle lead used in the SCS system of FIG. 2.

Referring further to FIG. 3, the IPG 14 comprises an outer case 40 for housing the electronic and other components (described in further detail below), and a connector 42 in which the proximal end of the stimulation lead 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 serves as an electrode.

As will be described in further detail below, the IPG 14 includes pulse generation circuitry that provides electrical conditioning and stimulation energy to the electrodes 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), and pulse rate (measured in pulses per second). With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case, so that the electrical current has a path from the energy source contained within the IPG case to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes is activated along with the case of the IPG 14, so that electrical energy is transmitted between the selected electrode and case. Monopolar delivery may also occur when one or more of the lead electrodes are activated along with a large group of lead electrodes located remotely from the one more lead electrodes so as to create a monopolar effect; that is, electrical energy is conveyed from the one or more lead electrodes in a relatively isotropic manner. Multipolar delivery occurs when two or more of the lead electrodes are activated as anode and cathode, so that electrical energy is transmitted between the selected electrodes.

As best illustrated in FIG. 3, the stimulation lead 12 takes the form of a surgical paddle lead that comprises an elongated body 44 having a proximal end 46 and a distal end 48, and a paddle-shaped membrane 50 formed at the distal end 48 of the lead body 44. In an alternative embodiment, the stimulation lead 12 may include multiple elongated bodies, in which case, the paddle-shaped membrane 50 may be formed at the distal ends of the elongated bodies. The lead body 44 may, e.g., have a diameter within the range of 0.03 inches to 0.07 inches and a length within the range of 30 cm to 90 cm for spinal cord stimulation applications. Each lead body 44 may be composed of a suitable electrically insulative material, such as, a polymer (e.g., polyurethane or silicone), and may be extruded from as a unibody construction. The paddle-shaped membrane 50 is composed of an electrically insulative material, such as silicone.

The stimulation lead 12 further comprises a plurality of terminals (not shown) mounted to the proximal end 46 of the lead body 44 and the plurality of electrodes 26 disposed on one side of the exterior surface of the paddle-shaped membrane 50 in a two-dimensional arrangement. Further details regarding the construction and method of manufacture of paddle leads are disclosed in U.S. patent application Ser. No. 11/319,291, entitled "Stimulator Leads and Methods for Lead Fabrication," the disclosure of which is expressly incorporated herein by reference.

Significant to some of the present invention, the electrodes 26 are arranged in four columns along the longitudinal axis of the stimulation lead 12. In particular, the electrodes 26 are arranged in two inner columns of electrodes 26' that are immediately adjacent to each other, and two outer columns of electrodes 26" that flank and are immediately adjacent the respective inner electrode columns 26'. For the purposes of this specification, two electrode columns are immediately adjacent to each other if no electrode column is disposed between the respective electrode columns. As will be described in further detail below, the use of four or more electrode columns allows the locus of stimulation energy to be adjusted in the transverse direction, as well as provides the option of electronically selecting wider or narrower cathode-anode spacings. Each of the electrodes 26 is composed of an electrically conductive, non-corrosive, material, such as, e.g., platinum, titanium, stainless steel, or alloys thereof.

The stimulation lead 12 also includes a plurality of electrical conductors (not shown) extending through the lead body 44 and connected between the respective terminals (not shown) and electrodes 26 using suitable means, such as welding, thereby electrically coupling the proximally-located terminals with the distally-located electrodes 26. In the case where the stimulation lead 12 includes multiple elongated bodies, the proximally-located terminals on each lead body will be electrically coupled to a specific column of electrodes 26 located on the paddle-shaped membrane 50. In alternative embodiments, the electrodes 26 may be arranged in more than four columns. For example, if five columns are used, there may be three inner electrode columns, and two outer electrode columns flanking the three inner electrode columns.

Although the stimulation lead 12 is shown as having sixteen electrodes 26, the number of electrodes may be any number suitable for the application in which the stimulation lead 12 is intended to be used (e.g., four, eight, twelve, twenty, etc.), as long as there are at least four electrodes extending along the paddle-shaped membrane 50 in a direction transverse to the longitudinal axis of the stimulation lead 12.

In the embodiment illustrated in FIG. 3, each of the electrodes 26 has a rectangular shape, with the longest dimension of the electrode being oriented along the longitudinal axis of the stimulation lead 12, and the shortest dimension of the electrode being oriented transverse to the longitudinal axis of the stimulation lead 12. In this manner, the electrodes 26 may be more easily arranged on the paddle-shaped membrane 50, which has a similar aspect ratio as the electrodes 26. Alternatively, the electrodes 26 may be square, circular, oblong, elliptical, or circular. Furthermore, the electrodes 26 may have non-uniform shapes (e.g., some may be rectangular, and others may be elliptical). In the illustrated embodiment, each electrode may have a longitudinal dimension in the range of 1.0-4.0 mm, and a transverse dimension in the range of 0.5-2.5 mm. Immediately adjacent electrode columns may have a transverse spacing 52 (as measured between the centers of the columns) in the range of 1.5-4.0 mm, and immediately adjacent electrodes in each column may have a longitudinal spacing 54 (as measured between the centers of the electrodes) in the range of 1.5-4.0 mm. Preferably, a transverse spacing 56 between the outer electrode columns (as measured between the centers of the columns) is in the range of 4.5-11.0 mm. Ultimately, the transverse and longitudinal spacings between immediately adjacent electrodes should be small enough, so that activation of electrodes will have a spatially combined effect.

Figure 4:
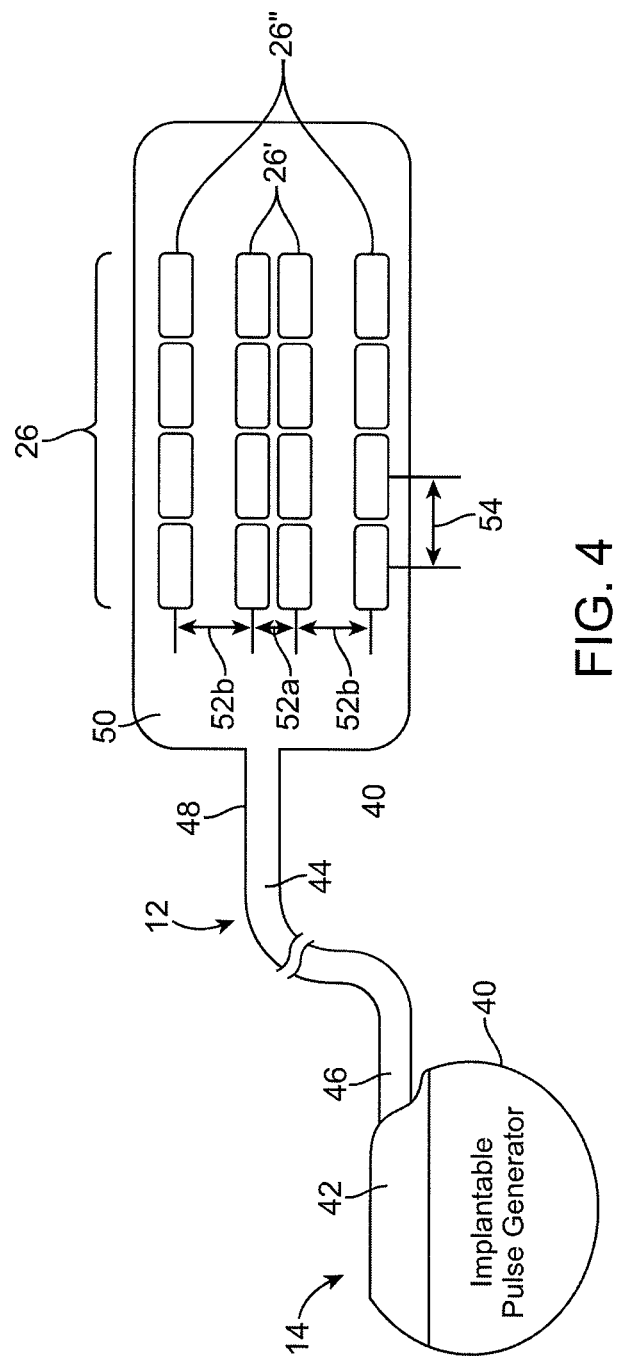
FIG. 4 is a profile view of an implantable pulse generator (IPG) and another embodiment of neurostimulation paddle lead used in the SCS system of FIG. 2.

Although the electrode columns of the stimulation paddle lead 12 illustrated in FIG. 3 are shown as having uniform transverse spacings, it may be advantageous to vary the transverse spacings between the electrode columns. For example, referring to FIG. 4, the inner transverse spacing 52*a* between the inner electrode columns 26' may be less than the outer transverse spacings 52*b* between each inner electrode column 26' and the respective adjacent outer electrode column 26". Preferably, the ratio between the inner spacing and the outer spacings is within the range of 0.10-0.75. As will be described in further detail below, this configuration provides an optimum compromise between selectivity of the locus of the stimulation energy and the avoidance of inadvertent stimulation of dorsal root (DR) fibers. Alternatively, if stimulation of the DR fibers is desired, the inner transverse spacing 52*a* between the inner electrode columns 26' may be more than the outer transverse spacings 52*b* between each inner electrode column 26' and the respective adjacent outer electrode column 26".

Although the electrode columns of the stimulation paddle lead 12 illustrated in FIG. 2 are shown as being longitudinally aligned with each other (i.e., they are not offset from each other in the longitudinal direction), it may be advantageous to offset some of the electrode columns from each other. For example, referring to FIG. 5, the inner electrode columns 26' are longitudinally offset from the other outer electrode columns 26" (i.e., the electrode columns 26' are not at the same longitudinal level). As there shown, only three electrodes 26 are disposed within each inner electrode column 26'. In the embodiment illustrated in FIG. 5, each electrode in the inner electrode columns 26' is equi-distant to the two immediately adjacent electrodes in the respective outer electrode column 26" (i.e., the outer electrode just above and the outer electrode just below the respective inner electrode). As will be described in further detail below, longitudinally offsetting the electrode columns in this manner provides for a more efficient use of the stimulation energy to stimulate dorsal column (DC) fibers while preventing the inadvertent stimulation of dorsal root (DR) fibers.

Figure 6:
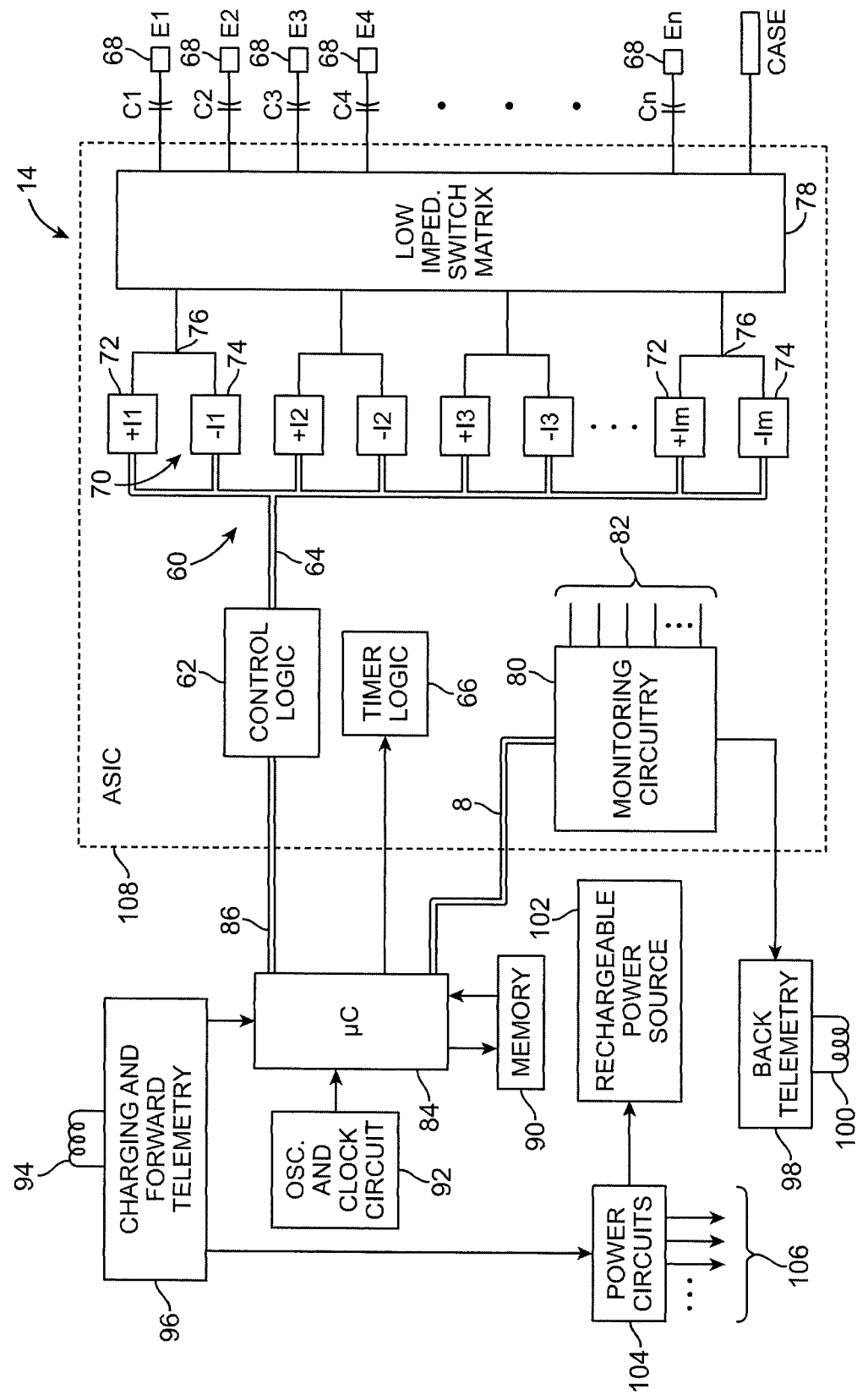
FIG. 6 is a block diagram of the internal components of an IPG used in the SCS system of FIG. 2.

Turning next to FIG. 6, one exemplary embodiment of the IPG 14 (and alternatively the ETS 20) will now be described. The IPG 14 includes stimulation output circuitry 60 configured for generating electrical stimulation energy in accordance with a defined pulsed waveform having a specified pulse amplitude, pulse rate, and pulse duration under control of control logic circuitry 62 over data bus 64. Control of the pulse rate and pulse duration of the electrical waveform is facilitated by timer logic circuitry 66, which may have a suitable resolution, e.g., 10 µs. The stimulation energy generated by the stimulation output circuitry 60 is output via capacitors C1-C16 to electrical terminals 68 corresponding to electrodes E1-E16.

In the illustrated embodiment, the stimulation output circuitry 60 comprises a plurality m independent current source pairs 70 capable of supplying stimulation energy to the electrical terminals 68 at a specified and known amperage. One current source 72 of each pair 70 functions as a positive (+) or anodic current source, while the other current source 74 of each pair 70 functions as a negative (−) or cathodic current source. The outputs of the anodic current source 72 and the cathodic current source 74 of each pair 70 are connected to a common node 76. The stimulation output circuitry 60 further comprises a low impedance switching matrix 78 through which the common node 76 of each current source pair 70 is connected to any of the electrical terminals 68 via the capacitors C1-C16.

Thus, for example, it is possible to program the first anodic current source 72 (+I1) to produce a pulse having a peak amplitude of +4 mA (at a specified rate and for a specified duration), and to synchronously program the second cathodic current source 74 (−I2) to similarly produce a pulse having a peak amplitude of −4 mA (at the same rate and pulse duration), and then connect the node 76 of the anodic current source 72 (+I1) to the electrical terminal 68 corresponding to electrode E3, and connect the node 76 of the cathodic current source 74 (−I2) to the electrical terminal 68 corresponding to electrode E1.

Hence, it is seen that each of the programmable electrical terminals 68 can be programmed to have a positive (sourcing current), a negative (sinking current), or off (no current)

polarity. Further, the amplitude of the current pulse being sourced or sunk from a given electrical terminal 68 may be programmed to one of several discrete levels. In one embodiment, the current through each electrical terminal 68 can be individually set from 0 to ±10 mA in steps of 100 μA, within the output voltage/current requirements of the IPG 14. Additionally, in one embodiment, the total current output by a group of electrical terminals 68 can be up to ±20 mA (distributed among the electrodes included in the group). Moreover, it is seen that each of the electrical terminals 68 can operate in a multipolar mode, e.g., where two or more electrical terminals are grouped to source/sink current at the same time. Alternatively, each of the electrical terminals 68 can operate in a monopolar mode where, e.g., the electrical terminals 68 are configured as cathodes (negative), and case of the IPG 14 is configured as an anode (positive).

It can be appreciated that an electrical terminal 68 may be assigned an amplitude and included with any of up to k possible groups, where k is an integer corresponding to the number of timing channels, and in one embodiment, is equal to 4, and with each timing channel k having a defined pulse amplitude, pulse duration, and pulse rate. Other timing channels may be realized in a similar manner. Thus, each channel identifies which electrical terminals 68 (and thus electrodes) are selected to synchronously source or sink current, the pulse amplitude at each of these electrical terminals, and the pulse duration, and pulse rate.

The IPG 14 further comprises monitoring circuitry 80 for monitoring the status of various nodes or other points 82 throughout the IPG 14, e.g., power supply voltages, temperature, battery voltage, and the like. The monitoring circuitry 80 is also configured for measuring electrical data at the electrodes 26 (e.g., electrode impedance and/or electrode field potential) necessary to determine whether each of the electrodes 26 is functioning properly and is properly coupled to the IPG 14. In cases where the electrode array 12 is used to sense physiological information, the monitoring circuitry 80 may also have the appropriate circuitry (e.g., an analog/digital converter) for converting the physiological information sensed by the electrodes 26 into a form that can be subsequently analyzed. The physiological information at the electrodes 26 may be measured using any one of a variety of means, but preferably is made independent of the electrical stimulation pulses, as described in U.S. Pat. Nos. 6,516,227 and 6,993,384, which are expressly incorporated herein by reference.

The IPG 14 further comprises processing circuitry in the form of a microcontroller (μC) 84 that controls the control logic circuitry 62 over data bus 86, and obtains status data, and optionally physiological information, from the monitoring circuitry 80 via data bus 88. The IPG 14 additionally controls the timer logic circuitry 66. The IPG 14 further comprises memory 90 and an oscillator and clock circuit 92 coupled to the microcontroller 84. Thus, the microcontroller 84, in combination with the memory 90 and oscillator and clock circuit 92, comprise a microprocessor system that carries out functions in accordance with a suitable program stored in the memory 90. Alternatively, for some applications, the functions provided by the microprocessor system may be carried out by a suitable state machine.

The microcontroller 84 generates the necessary control and status signals, which allow the microcontroller 84 to control the operation of the IPG 14 in accordance with the operating program and stimulation parameters stored in the memory 90. In controlling the operation of the IPG 14, the microcontroller 84 is able to individually generate stimulus pulses at the electrodes 26 using the stimulation output circuitry 60, in combination with the control logic circuitry 62 and timer logic circuitry 66, thereby allowing each electrode 26 to be paired or grouped with other electrodes 26, including the monopolar case electrode, and to control and modify the polarity, pulse amplitude, pulse rate, pulse duration, and channel through which the current stimulus pulses are provided.

In the case wherein the IPG 14 processes physiological information (either sensed at the electrodes 26 via the monitoring circuitry 80 or sensed using a separate monitor), the algorithm used to electronically displace the locus of the stimulation region based on the sensed physiological information may be stored in the memory 90 for execution by the microcontroller 84 to appropriately control the stimulation output circuitry 60 via adjustment of the stimulation parameters. In this case, the microcontroller 84 will determine the stimulation parameters, including the electrode combination and individual amplitudes of the electrical energy at the electrodes 26, necessary to electronically displace the locus of the stimulation region in an optimum or otherwise more effective manner, and control the stimulation output circuitry 60 in accordance with these stimulation parameters.

The IPG 14 further comprises an alternating current (AC) receiving coil 94 for receiving programming data (e.g., the operating program and/or stimulation parameters) from the RC 16 in an appropriate modulated carrier signal, and charging and forward telemetry circuitry 96 for demodulating the carrier signal it receives through the AC receiving coil 94 to recover the programming data, which programming data is then stored within the memory 90, or within other memory elements (not shown) distributed throughout the IPG 14.

The IPG 14 further comprises back telemetry circuitry 98 and an alternating current (AC) transmission coil 100 for sending informational data sensed through the monitoring circuitry 80 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 102 and power circuits 104 for providing the operating power to the IPG 14. The rechargeable power source 102 may, e.g., comprise a lithium-ion or lithium-ion polymer battery. The rechargeable battery 102 provides an unregulated voltage to the power circuits 104. The power circuits 104, in turn, generate the various voltages 106, some of which are regulated and some of which are not, as needed by the various circuits located within the IPG 14. The rechargeable power source 102 is recharged using rectified AC power (or DC power converted from AC power through other means, e.g., efficient AC-to-DC converter circuits, also known as "inverter circuits") received by the AC receiving coil 104. To recharge the power source 102, an external charger (not shown), which generates the AC magnetic field, is placed against, or otherwise adjacent, to the patient's skin over the implanted IPG 14. The AC magnetic field emitted by the external charger induces AC currents in the AC receiving coil 104. The charging and forward telemetry circuitry 96 rectifies the AC current to produce DC current, which is used to charge the power source 102. While the AC receiving coil 104 is described as being used for both wirelessly receiving communications (e.g., programming and control data) and charging energy from the external device, it should be appreciated that the AC receiving coil 104 can be arranged as a dedicated charging coil, while another coil, such as coil 100, can be used for bi-directional telemetry.

As shown in FIG. 6, much of the circuitry included within the IPG 14 may be realized on a single application specific integrated circuit (ASIC) 108. This allows the overall size of the IPG 14 to be quite small, and readily housed within a suitable hermetically-sealed case. Alternatively, most of the circuitry included within the IPG 14 may be located on multiple digital and analog dies, as described in U.S. patent application Ser. No. 11/177,503, filed Jul. 8, 2005, which is incorporated herein by reference in its entirety. For example, a processor chip, such as an application specific integrated circuit (ASIC), can be provided to perform the processing functions with on-board software. An analog IC (AIC) can be provided to perform several tasks necessary for the functionality of the IPG 14, including providing power regulation, stimulus output, impedance measurement and monitoring. A digital IC (DigIC) may be provided to function as the primary interface between the processor IC and analog IC by controlling and changing the stimulus levels and sequences of the current output by the stimulation circuitry in the analog IC when prompted by the processor IC.

It should be noted that the diagram of FIG. 6 is functional only, and is not intended to be limiting. Those of skill in the art, given the descriptions presented herein, should be able to readily fashion numerous types of IPG circuits, or equivalent circuits, that carry out the functions indicated and described. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to the stimulation lead 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 7:
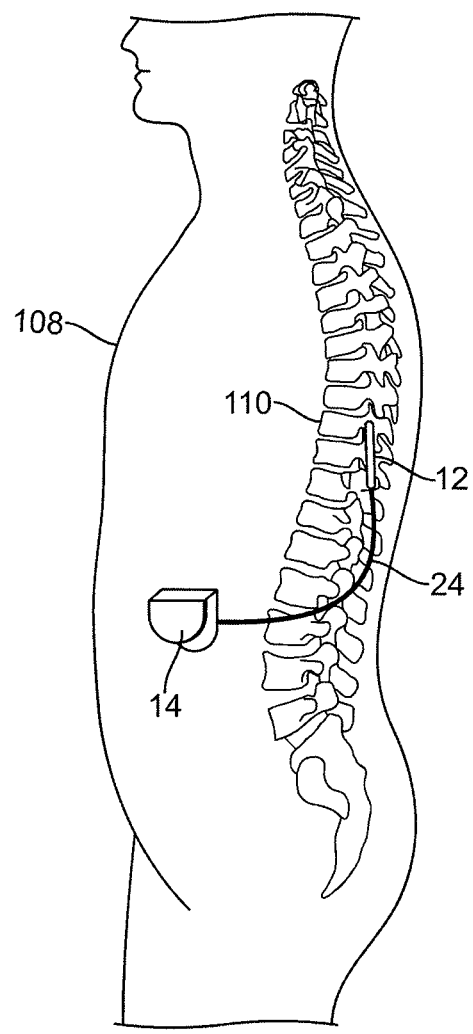
FIG. 7 is a plan view of the implantable components of the SCS system of FIG. 2 in use with a patient.

Referring to FIG. 7, the stimulation lead 12 is implanted within the spinal column 110 of a patient 108. The preferred placement of the stimulation lead 12 is adjacent, i.e., in the epidural space above the spinal cord area to be stimulated. Due to the lack of space near the location where the stimulation lead 12 exit the spinal column 110, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the stimulation lead 12. After implantation, the IPG 14 is used to provide the therapeutic stimulation under control of the patient.

Figure 5:
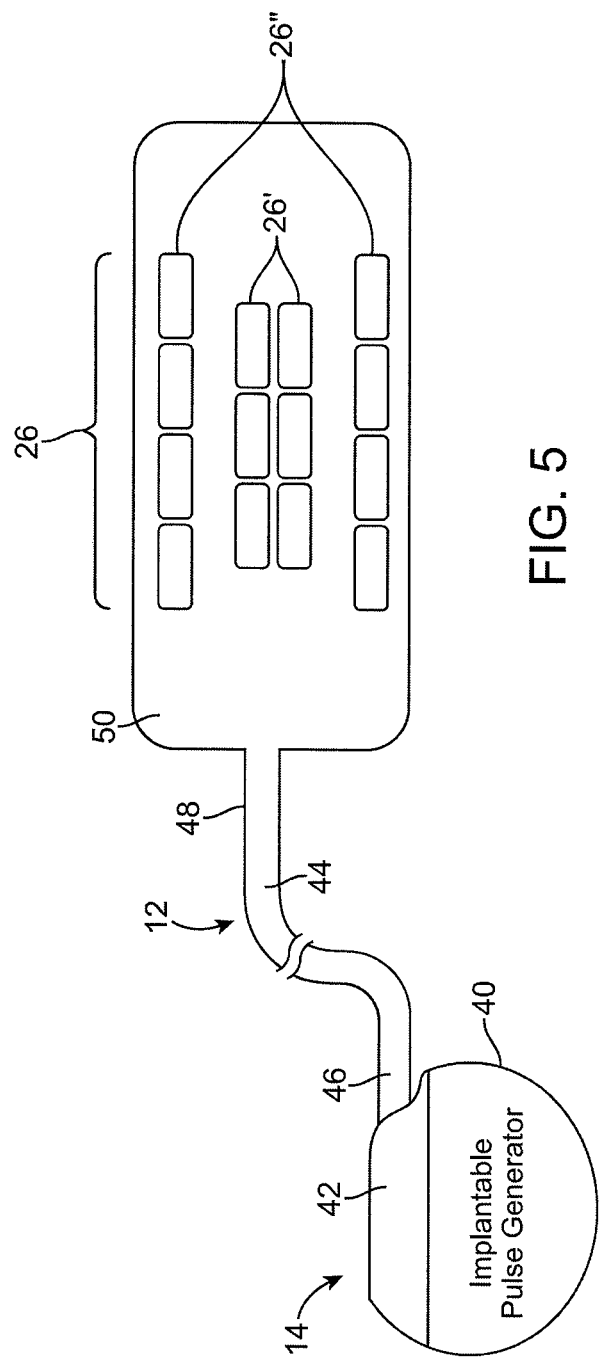
FIG. 5 is a profile view of an implantable pulse generator (IPG) and still another embodiment of a neurostimulation paddle lead used in the SCS system of FIG. 2.
Figure 8:
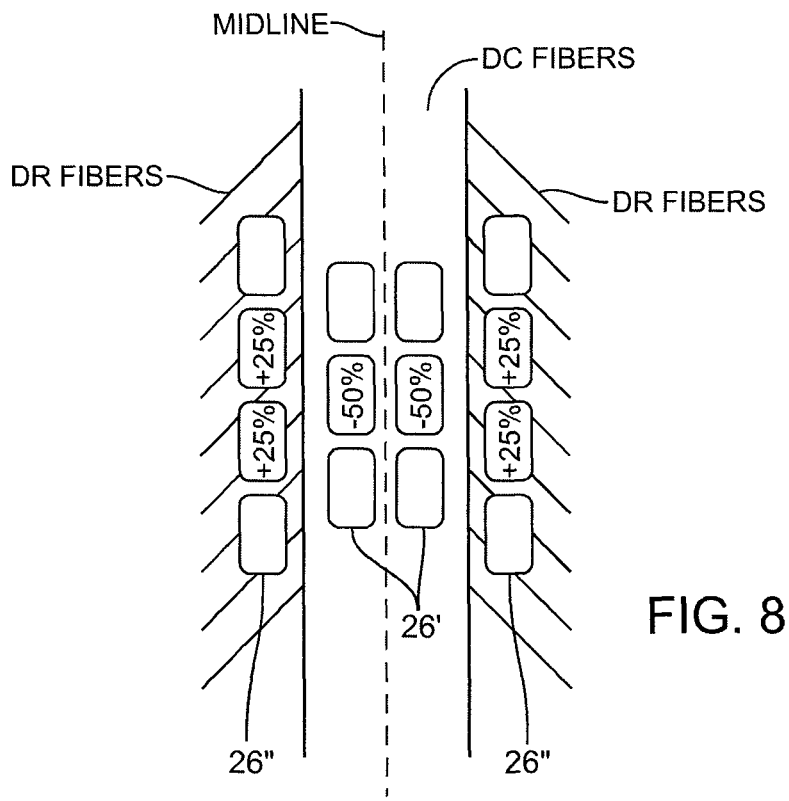
FIG. 8 is a coronal view of a cathode-anode electrode arrangement that can create a medial-lateral electrical field to stimulate spinal cord tissue using the neurostimulation paddle lead of FIG. 5.

Referring now to FIG. 8, the stimulation lead 12 may be implanted within the patient, such that the electrodes 26 are disposed adjacent the spinal cord, with the inner electrode columns 26' disposed directly over the dorsal column (DC) fibers, and the outer electrode columns 26" disposed directly over the dorsal root (DR) fibers. Notably, the stimulation lead 12 illustrated in FIG. 5 is used, so that the relatively small spacing between the inner electrode columns 26' maintains them away from the DR fibers to prevent the inadvertent stimulation of the DR fibers. The relatively large spacing between the inner electrode columns 26' and the respective outer electrode columns 26" places the outer electrode columns 26" directly over the DR fibers to guard against overstimulation of the DR fibers.

In particular, the IPG 14 may configure at least one of the electrodes in the inner electrode columns 26' as a cathode, and at least one of the electrodes in the outer electrode columns 26" as an anode, such that electrical stimulation energy conveyed from the IPG 14 between the cathode(s) and anode(s) creates a medial-lateral electrical field that stimulates the DC fibers, while preventing stimulation of the DR fibers. That is, electrical energy originating from the cathode(s) stimulates the DC fibers, while the anode(s) "push" the electrical stimulation energy away from the DR fibers. For the purposes of this specification, a "medial-lateral field" means that the strongest field components are oriented approximately parallel to the medial-lateral axis, as opposed to a "rostral-caudal field," which means that the strongest field components are oriented approximately parallel to the rostral-caudal axis.

In the electrode arrangement illustrated in FIG. 8, the IPG 14 configures a single row of inner electrodes 26' (i.e., two immediately adjacent and longitudinally aligned electrodes of the respective inner electrode columns 26') as cathodes (cathodes shown with "c"), while configuring the two rows of outer electrodes 26" that flank the cathodes (i.e., the two immediately adjacent electrodes of the left outer electrode column 26" that longitudinally flank the cathode in the left inner electrode column 26' and the two immediately adjacent electrodes of the right outer electrode column 26" that longitudinally flank the cathode in the right inner electrode column 26') as anodes (anodes shown with "a"). The IPG 14 further configures the cathodes to have a fractionalized cathodic current of 50% each, and the anodes to have a fractionalized anodic current of 25% each. Thus, in the case where the midline of the spinal cord is equidistant between the cathodes, the locus of the applied electrically energy will be located on the midline of the spinal cord. Of course, if midline of the spinal cord is offset from the cathodes, the locus of the applied electrical energy will be located offset from the midline of the spinal cord, which may be desired in some circumstances.

Figure 9:
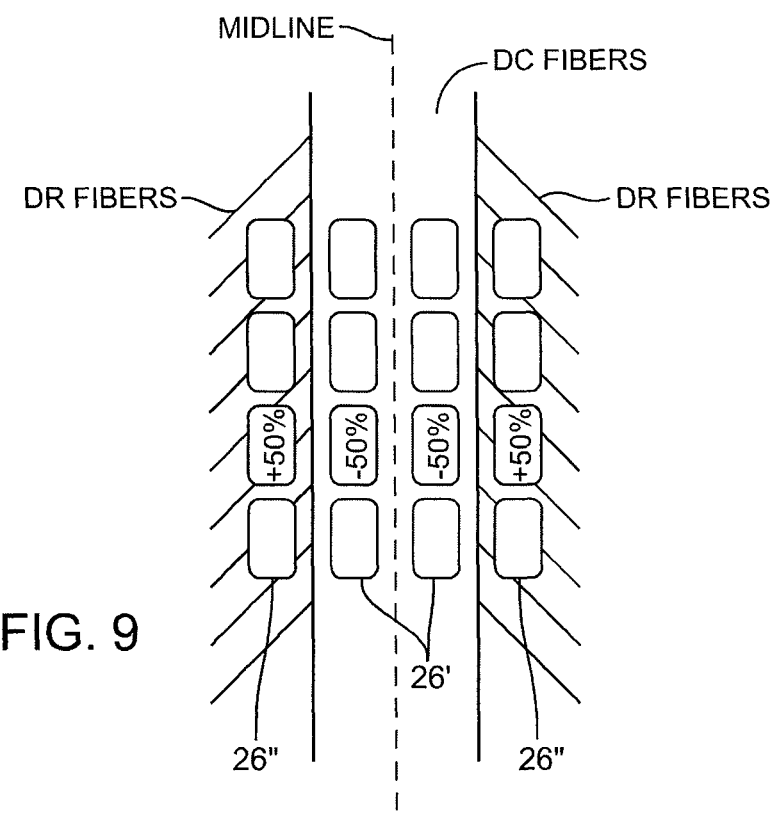
FIG. 9 is a coronal view of a cathode-anode electrode arrangement that can create a medial-lateral electrical field to stimulate spinal cord tissue using the neurostimulation paddle lead of FIG. 3.

Notably, as compared to a cathode-anode configuration used with the stimulation lead 12 illustrated in FIG. 2 or 3 in which a single row of electrodes may be activated (two adjacent electrodes in the inner electrode columns 26' being configured as cathodes, and an adjacent electrode in each of the outer electrode columns 26" being configured as anodes), as illustrated in FIG. 9, it has been discovered that the particular cathode-anode configuration illustrated in FIG. 8 provides a relatively efficient stimulation. Although each of the anodes in the cathode-anode configuration illustrated in FIG. 8 has a fractionalized anodic current that is less than each of the anodes in the cathode-anode configuration illustrated in FIG. 9, thereby providing somewhat less of a guarding effect against overstimulation of the DR fibers, the cathodes in the cathode-anode configuration illustrated in FIG. 8 shunt less cathodic current than the cathodes in the cathode-anode configuration illustrated in FIG. 9, because the anode is more distributed. With appropriate geometries, the reduction in the guarding effect is smaller than the improvement in the shunting effect, yielding improved efficiency.

The electrodes in the arrangement illustrated in FIG. 8 can be variously configured to transversely adjust the locus of the stimulation energy, as well as to provide varying depths of electrical stimulation. In one method, immediately adjacent electrodes in the left and right inner electrode columns 26' may be configured as cathodes, and two adjacent electrodes that longitudinally flank the cathodes in only one of the outer electrode columns 26" may be configured as anodes. In this case, the anodes in one of the left or right outer electrode columns 26" are used to "push" the locus of the stimulation energy towards the other of the left or right outer electrode columns 26".

Figure 10A:
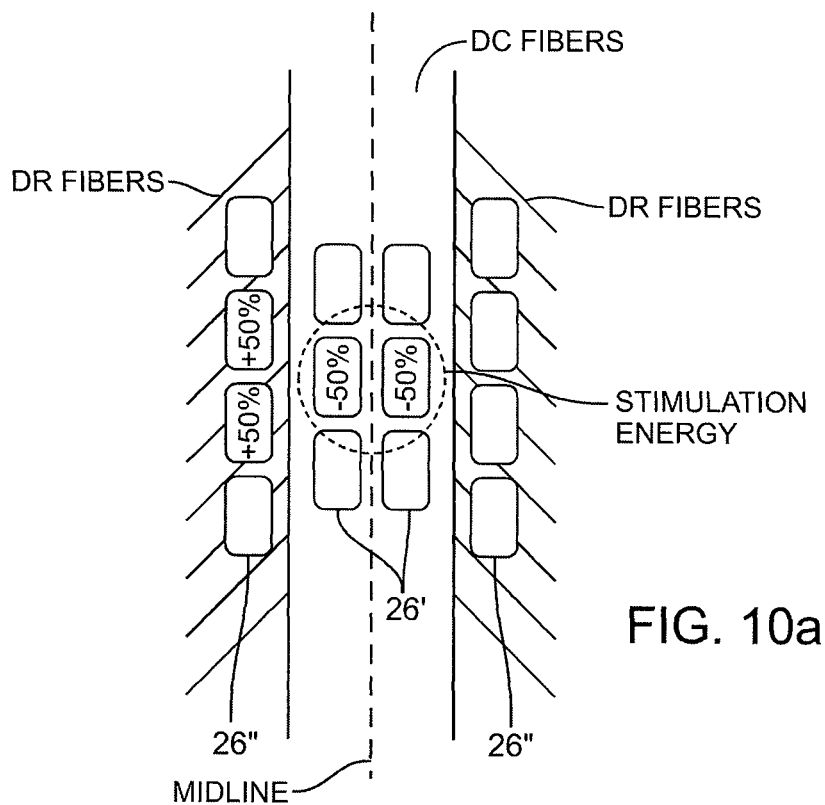
FIGS. 10a-10d are coronal views of different cathode-anode electrode arrangements that can create different medial-lateral electrical fields to stimulate spinal cord tissue using the neurostimulation paddle lead of FIG. 5.

For example, in a cathode-anode configuration illustrated in FIG. 10*a*, a single row of the electrodes in the inner electrode columns 26' (two immediately adjacent and longitudinally aligned electrodes) are configured as cathodes (with a fractionalized cathodic current of 50% each), and two immediately adjacent and longitudinally flanking electrodes in the left outer electrode column 26" are configured as anodes (with a fractionalized anodic current of 50% each). In this case, the anodes "push" the locus of stimulation energy towards the inactivated outer electrode column 26" (i.e., the right outer electrode column 26").

In another method, an electrode in only one of the left and right inner electrode columns 26' may be configured as a cathode, and two adjacent electrodes that longitudinally flank the cathodes in only one or in both of the outer electrode columns 26" may be configured as anodes. In these cases, the cathode in one of the left or right outer electrode columns 26" is used to shift the locus of the stimulation energy towards the one left or right outer electrode column 26". If the electrodes in both of the outer electrode columns 26" are configured as anodes, they will not serve to "push" the locus of stimulation energy, but will merely serve to guard both the left and right dorsal root (DR) fibers from stimulation.

Figure 10B:
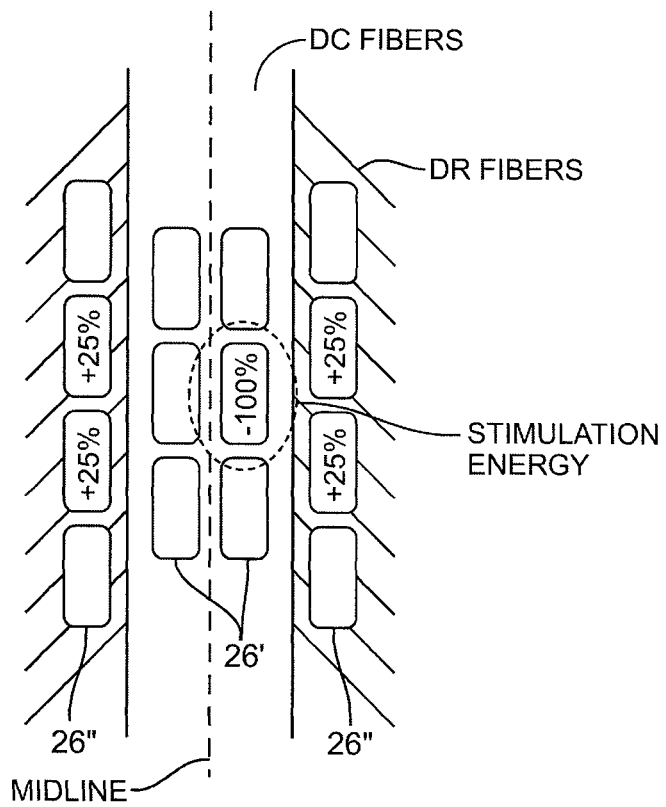

For example, in a cathode-anode configuration illustrated in FIG. 10*b*, a single electrode in the right inner electrode column 26' is configured as a cathode, and two immediately adjacent and longitudinally flanking electrodes in the left outer electrode column 26" and in the right outer electrode column 26" are configured as anodes (with a fractionalized anodic current of 25% each). In this case, the single cathode shifts the locus of stimulation energy to the right of the midline of the dorsal column (DC), and the anodes guard the DR fibers against stimulation.

Figure 10C:
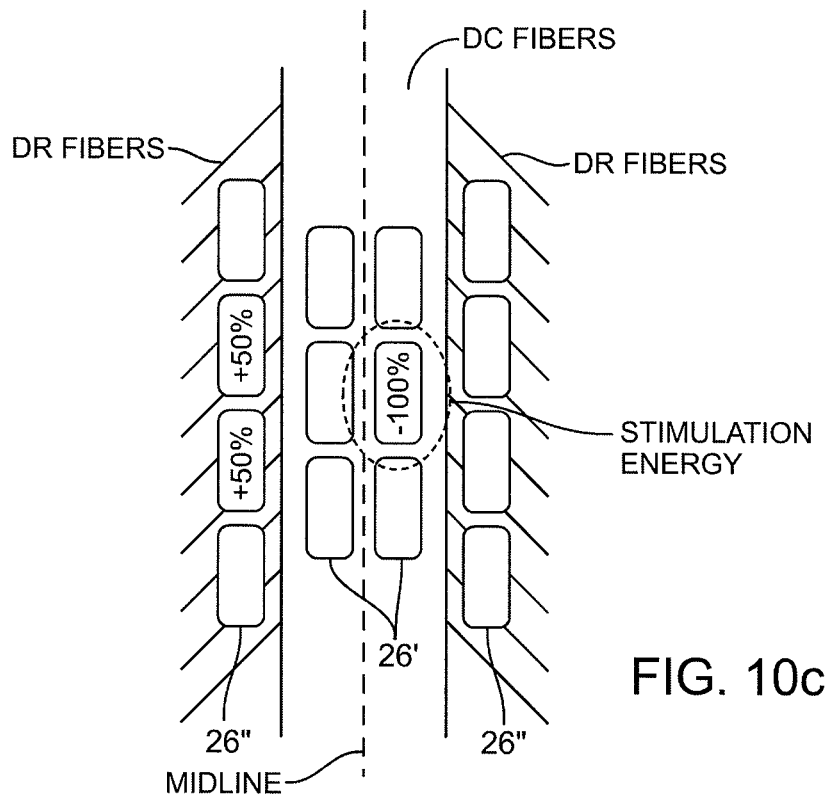

If the electrodes in only one of the outer electrode columns 26" are configured as anodes, they will serve to "push" the locus of stimulation energy towards the other outer electrode column 26". For example, in a cathode-anode configuration illustrated in FIG. 10*c*, a single electrode in the right inner electrode column 26' is configured as a cathode, and two immediately adjacent and longitudinally flanking electrodes in the left outer electrode column 26" are configured as anodes (with a fractionalized anodic current of 50% each). In this case, the single cathode moves the locus of stimulation energy to the right of the midline of the spinal cord, and the anodes further "push" the locus of stimulation energy towards the inactivated right outer electrode column 26".

In the case where the electrodes in both of the outer electrode columns 26" are configured as anodes, the electrodes in the outer electrode column 26" that are immediately adjacent to the only inner electrode column 26" in which the electrode is configured as a cathode can have a fractionalized current that is greater than the electrodes in the other outer electrode column 26" to further enhance their guarding effect with respect to the DR fibers that are closest to the activated cathode.

Figure 10D:
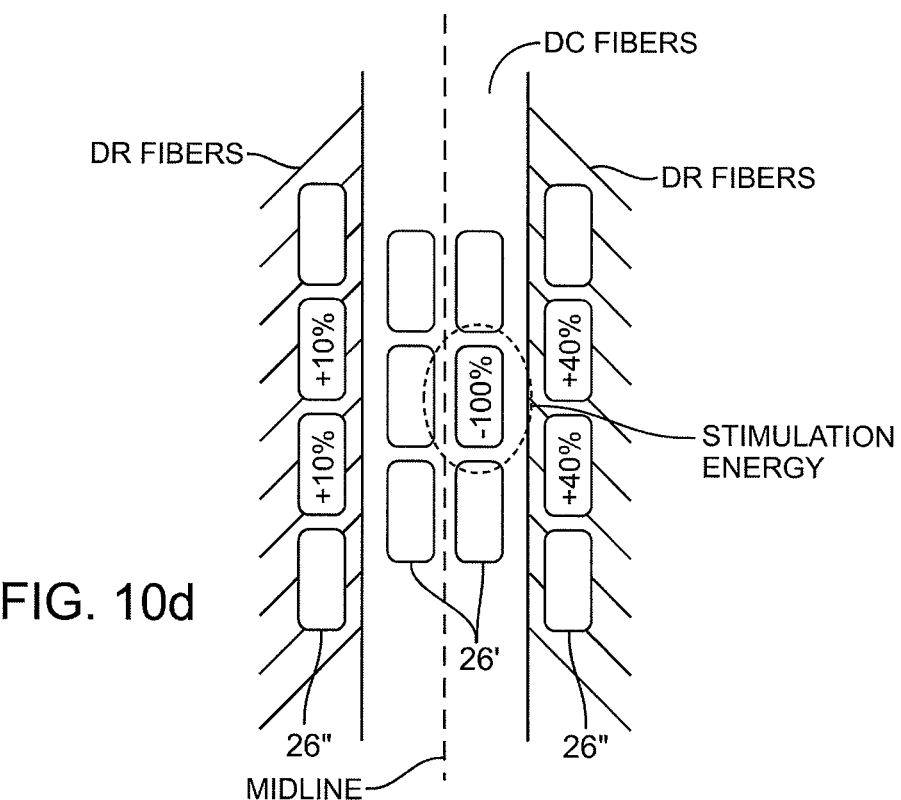

For example, in a cathode-anode configuration illustrated in FIG. 10*d*, a single electrode in the right inner electrode column 26' is configured as a cathode, and two immediately adjacent and longitudinally flanking electrodes in the left outer electrode column 26" and in the right outer electrode column 26" are configured as anodes (with a fractionalized anodic current of 10% for the left anodes, and a fractionalized anodic current of 40% for each of the right anodes). In this case, the single cathode moves the locus of stimulation energy to the right of the midline of the DC, the anodes in the left outer electrode column 26" guard the left DR fibers from stimulation, and the anodes in the right outer electrode column 26" guard the right DR fibers from stimulation. Notably, the fractionalized current for the anodes in the right electrode outer column 26" is greater than the fractionalized current for the anodes in the left electrode outer column 26", since the activated cathode is closer to the right DR fibers. Based on a modeled cathode-anode configuration that assumes a dCSF of 2.0 mm and a current output of 1.70 mA, a total of 1184 DC fibers were stimulated in the cathode-anode model of FIG. 9*d*.

The locus and size of the medial-lateral electrical field generated by the electrodes in the arrangement illustrated in FIG. 8 can be fine-tuned through the use of current steering. In doing this, the IPG 14 may first configure at least two electrodes in the inner electrode columns 26' as cathodes, and at least one electrode of each of the outer electrode columns 26" as anodes. The IPG 14 may then convey electrical energy between the cathodes and the anodes to create a medial-lateral electrical field that stimulates the spinal cord tissue (preferably stimulating the DC fibers without over-stimulating the DR fibers), and incrementally shifting cathodic current between the cathodes to modify the medial-lateral electrical field. Notably, for the purposes of this specification, current is incrementally shifted between two electrodes if the current is gradually shifted from one electrode to the other electrode over a few steps. Preferably, cathodic current is shifted between cathodes in increments equal to 10% or less. Navigation tables, such as those described in U.S. patent application Ser. No. 11/557,477, entitled "System and Method for Uniformly Displacing a Region of Neural Stimulation," which is expressly incorporated herein by reference, can be used to steer current between electrodes.

In one embodiment, the electrodes that are configured as cathodes are longitudinally aligned relative to each other (or rostral-caudally aligned relative to each other when implanted within the patient), such that incremental shifting of the current between the cathodes spatially shifts the medial-lateral electrical field transversely relative to the longitudinal axis (i.e., relative to the DC fibers of the spinal cord tissue).

Figure 11A:
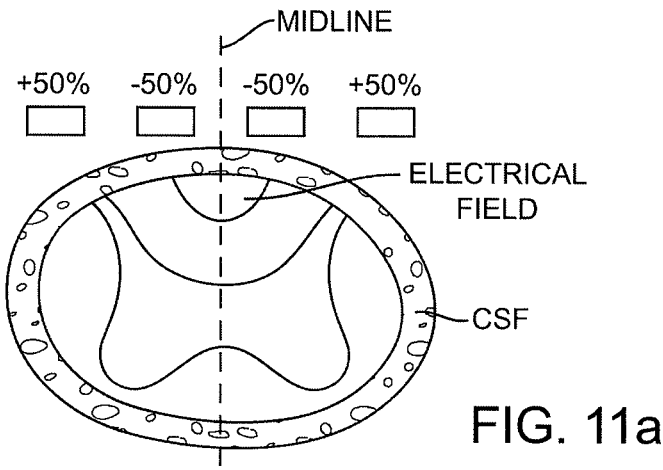
FIGS. 11a-11e are cross-sectional views of a cathode-anode electrode arrangement that can transversely steer a medial-lateral electrical field relative to spinal cord tissue using any of the neurostimulation paddle leads of FIGS. 3-5.
Figure 11B:
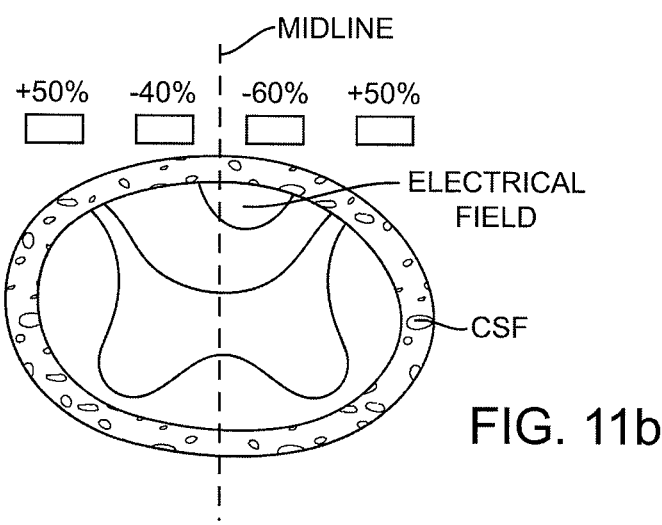
Figure 11C:
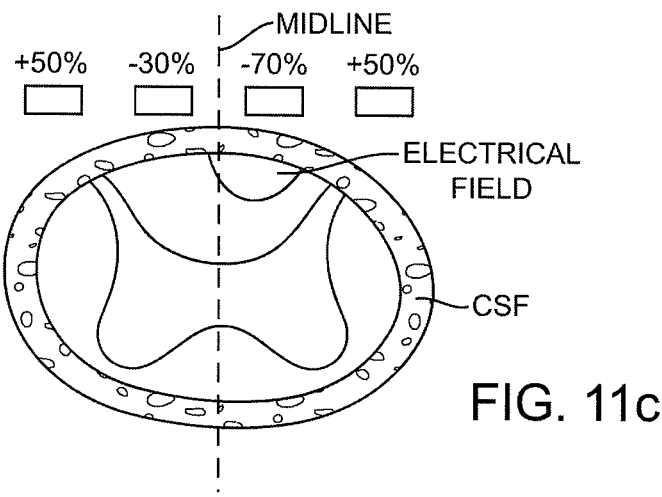

For example, initially assuming an equal distribution of cathodic current between the two cathodes (50% in each) (FIG. 11*a*), 10% of the cathodic current can be shifted from the left cathode to the right cathode (40% in left cathode and 60% in the right cathode)(FIG. 11*b*), thereby shifting the locus of the medial-lateral electrical field from the midline of the spinal cord tissue to a location offset to the right of the midline. 10% of the cathodic current can further be shifted from the left cathode to the right cathode (30% in left cathode and 70% in the right cathode) (FIG. 11*c*). The cathodic current can be shifted from the left cathode to the right cathode a number of times until none of the cathodic current flows through the left cathode and all of the cathodic current flows through the right cathode.

Figure 11D:
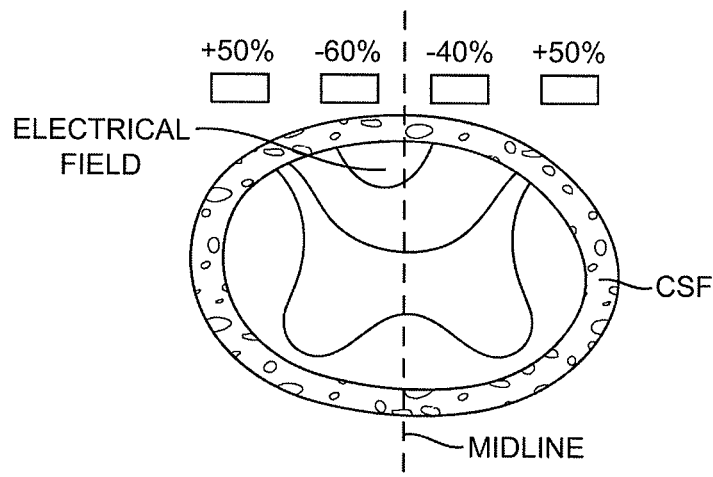
Figure 11E:
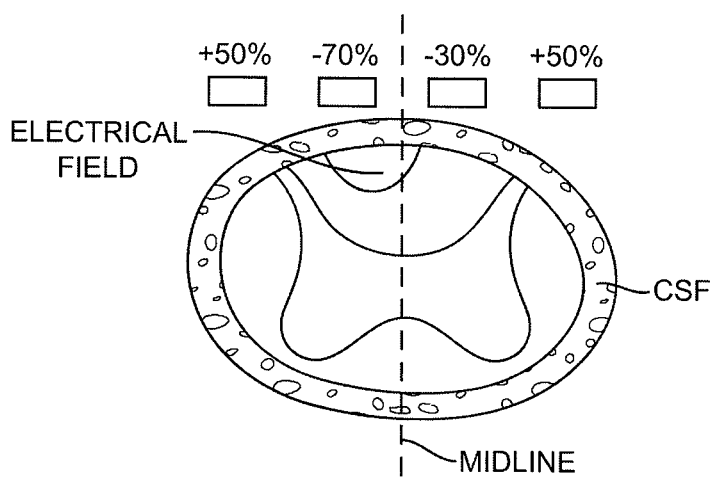

In a similar manner, initially assuming an equal distribution of cathodic current between the two cathodes (50% fractionalized current in each)(FIG. 11*a*), 10% of the cathodic current can be shifted from the right cathode to the left cathode (60% fractionalized current in left cathode and 40% fractionalized current in the right cathode)(FIG. 11*d*), thereby shifting the locus of the medial-lateral electrical field from the midline of the spinal cord tissue to a location offset to the left of the midline. 10% of the cathodic current can further be shifted from the right cathode to the left cathode (70% fractionalized current in left cathode and 30% fractionalized current in the right cathode) (FIG. 11*e*). The cathodic current can be shifted from the right cathode to the left cathode a number of times until none of the cathodic current flows through the right cathode and all of the cathodic current flows through the left cathode.

In another embodiment, the electrodes that are configured as cathodes are longitudinally offset from each other (i.e., rostral-caudally offset from each other), such that incremental shifting of the cathodic current between the cathodes expands the medial-lateral electrical field along the longitudinal axis (i.e., rostral-caudally expands the medial-lateral electrical field). This can be accomplished, e.g., when the dCSF is relatively large, thereby reducing the collective electrode impedance. When the dCSF is large enough, increasing the distribution of the current longitudinally among more electrodes will make little difference in the field at the spinal cord, but has improved collective impedance properties.

Figure 12A:
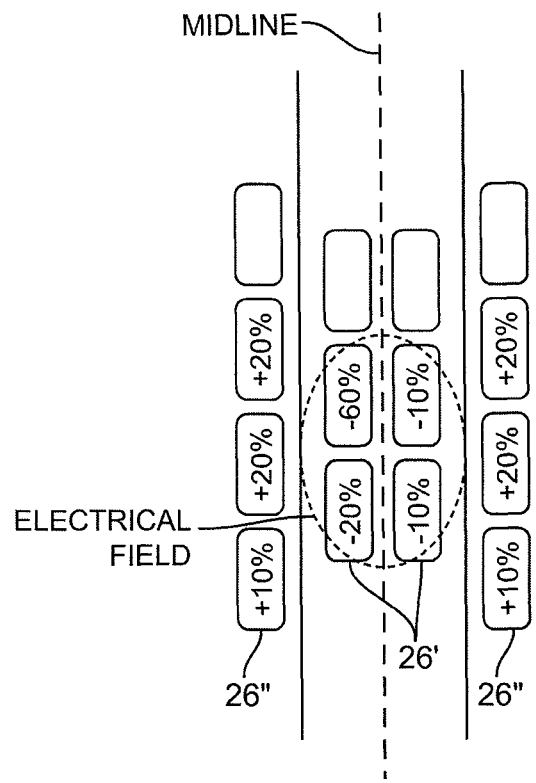
FIGS. 12a-12b are coronal views of different cathode-anode electrode arrangements that can rostral-caudally expand a medial-lateral electrical field relative to spinal cord tissue using the neurostimulation paddle lead of FIG. 5.

For example, referring to FIG. 12*a*, it is first assumed that four adjacent electrodes are configured with cathodes, with the bottom left cathode having a fractionalized current of 20%, the middle left cathode having a fractionalized current of 60%, the bottom right cathode having a fractionalized current of 10%, and the middle right cathode having a fractionalized current of 10%, and three anodes in each of the outer electrode columns are configured as anodes, with the bottom left anode having a fractionalized current of 10%, the middle left anode having a fractionalized current of 20%, the top left anode having a fractionalized current of 20%, the bottom right anode having a fractionalized current of 10%, the middle right anode having a fractionalized current of 20%, and the top right anode having a fractionalized current of 20%. Based on this configuration, the locus of the medial-lateral electrical field will be left of the midline and nearer the top cathodes.

Figure 12B:
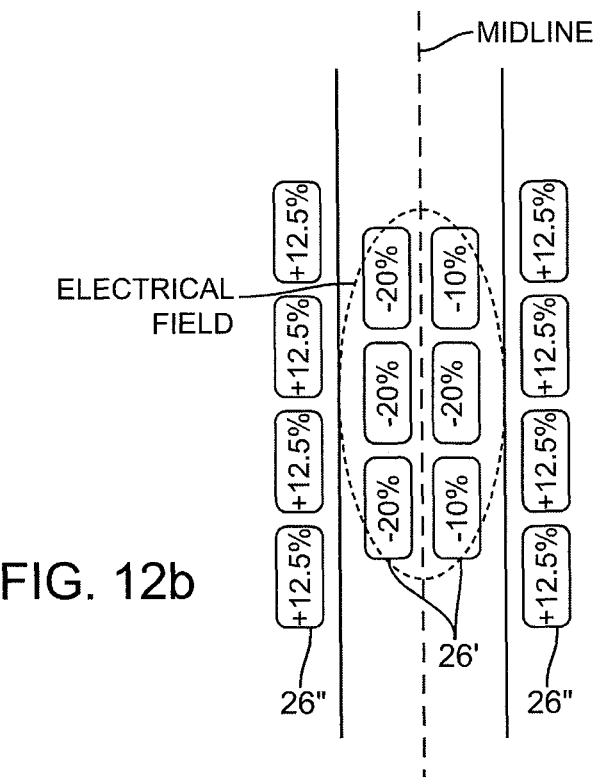

As shown in FIG. 12*b*, the medial-lateral electrical field can be expanded in the rostral direction by configuring an upper row of electrodes as cathodes, and incrementally shifting some of the current from the lower four cathodes to the upper two cathodes. In this case, some of the cathodic current is shifted to the upper cathodes, such that each of the left cathodes has a fractionalized current of 20%, the bottom right cathode has a fractionalized current of 10%, the middle right cathode has a fractionalized current of 20%, and the top right cathode has a fractionalized current of 10%. Anodic current is also shifted to the upper anodes, such that each of the anodes has a fractionalized current of 12.5%.

The electrode arrangement illustrated in FIG. 8 can also be reconfigured to selectively change the effective cathode-anode spacing. In doing this, the IPG 14 may configure a first one of electrodes in the inner electrode column 26' as a cathode, a second one of the electrodes in the inner electrode column 26' as one of a cathode and an anode, and two of the flanking electrodes in the respective outer electrode columns 26" as anodes. The IPG 14 may then convey electrical energy between the cathodes and the anodes to create a medial-lateral electrical field that stimulates the spinal cord tissue. The IPG 14 may then reconfigure the second inner electrodes as the other of the cathode and the anode, and reconveying electrical energy between the cathodes and the anodes to create a medial-lateral electrical field that stimulates the spinal cord tissue.

Figure 13A:
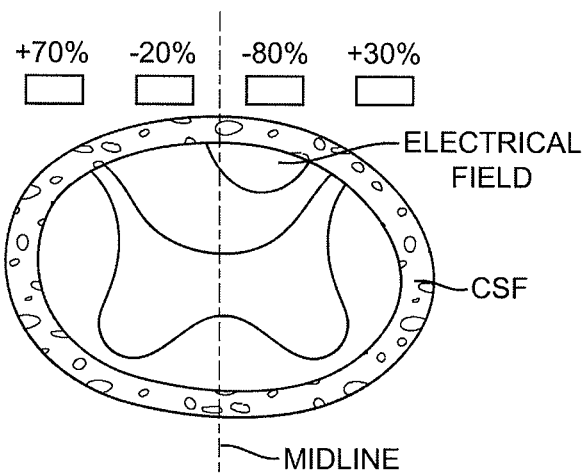
FIGS. 13a-13b are cross-sectional views of a cathode-anode electrode arrangement that can electrically modify the cathode-anode spacing using any of the neurostimulation paddle leads of FIGS. 3-5.
Figure 13B:
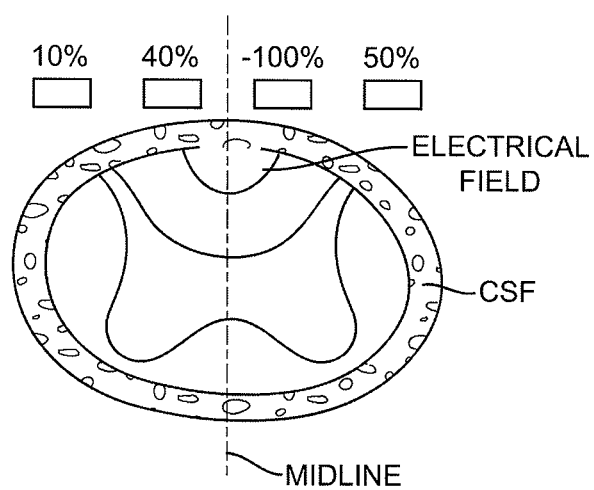

For example, referring to FIG. 13*a*, both of the inner electrodes are configured as cathodes, with the left cathode having a fractionalized current of 20%, and the right cathode having a fractionalized current of 80%, and both of the outer electrodes are configured as anodes, with the left anode having a fractionalized current of 70%, and the right anode having a fractionized current of 30%. In this case, the effective cathode-anode spacing will be relatively large, so that, in the case of a large dCSF, the interelectrode impedance will be reduced, thereby increasing the size of the electrical field. Referring to FIG. 13*b*, the left inner electrode is reconfigured as an anode, with the inner anode having a fractionalized current of 40%, the right cathode having a fractionalized current of 100%, the left outer anode having a fractionalized current of 10%, and the right outer anode having a fractionalized current of 50%. In this case, the effective cathode-anode spacing is relatively small, so that, in the case of a small dCSF, the medial-lateral electrical field can be more finely tuned.

The electrode arrangement illustrated in FIG. 8 can also be for stimulating the DC fibers on both lateral sides to the midline without stimulating DC fibers along the midline. In particular, the IPG 14 may convey electrical energy between the electrodes to create a medial-lateral electrical field having a locus on one lateral side of the midline of the spinal cord tissue (e.g., by configuring only a first one of the inner electrodes 26' as a cathode or configuring a first one of the inner electrodes 26' to have more cathodic current than a second one of the inner electrodes 26'), and conveying electrical energy between the electrodes to create a medial-lateral electrical field having a locus on the other lateral side of the midline of the spinal cord tissue (e.g., by configuring only a second one of the inner electrodes 26' as a cathode or configuring a second one of the inner electrodes 26' to have more cathodic current than a first one of the inner electrodes 26'). The IPG 14 may utilize two channels to repeatedly move the locus on of the medial-lateral electrical field back and forth between the left and right sides of the midline.

Figure 14A:
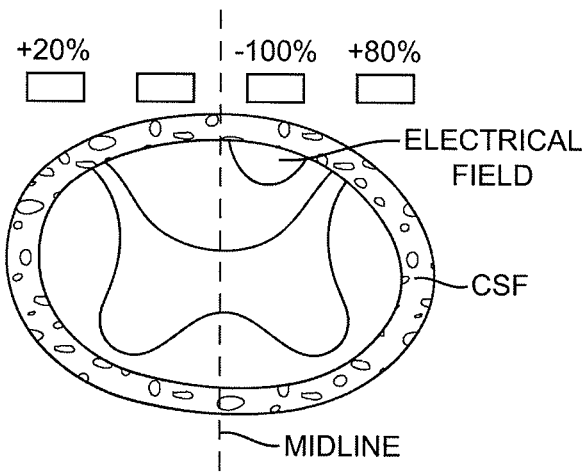
FIGS. 14a-14b are cross-sectional views of a cathode-anode electrode arrangement that can create different medial-lateral electrical fields on both sides of the midline of spinal cord tissue using any of the neurostimulation paddle leads of FIGS. 3-5.
Figure 14B:
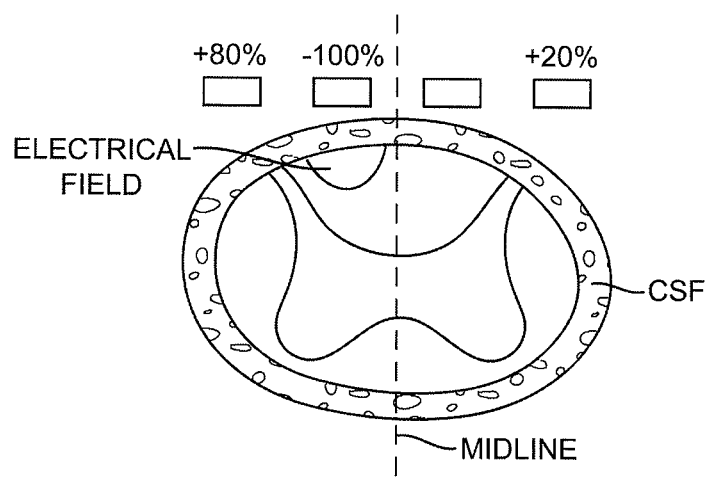

For example, referring to FIG. 14*a*, the right inner electrode is configured as a cathode, and the outer left and right flanking electrodes are configured as anodes, with the right cathode having all of the cathodic current, the left anode having a fractionalized anodic current of 20%, and the right anode having a fractionalized anodic current of 80%. In this case, the locus of the medial-lateral electrical field will be to the right of the midline. As a result, only the DC fibers on the right side of the midline will be stimulated. Referring to FIG. 14*b*, the left inner electrode is configured as a cathode, and the outer flanking electrodes are configured as anodes, with the left inner electrode having all of the cathodic current, the left outer electrode having a fractionalized anodic current of 80%, and the right outer electrode having a fractionalized anodic current of 20%. In this case, the locus of the medial-lateral electrical field will be to the left of the midline. As a result, only the DC fibers on the left side of the midline will be stimulated. Since some have hypothesized that low-back fibers are lateral to the midline, this system and method may be particularly useful for low-back fiber stimulation.

Figure 15:
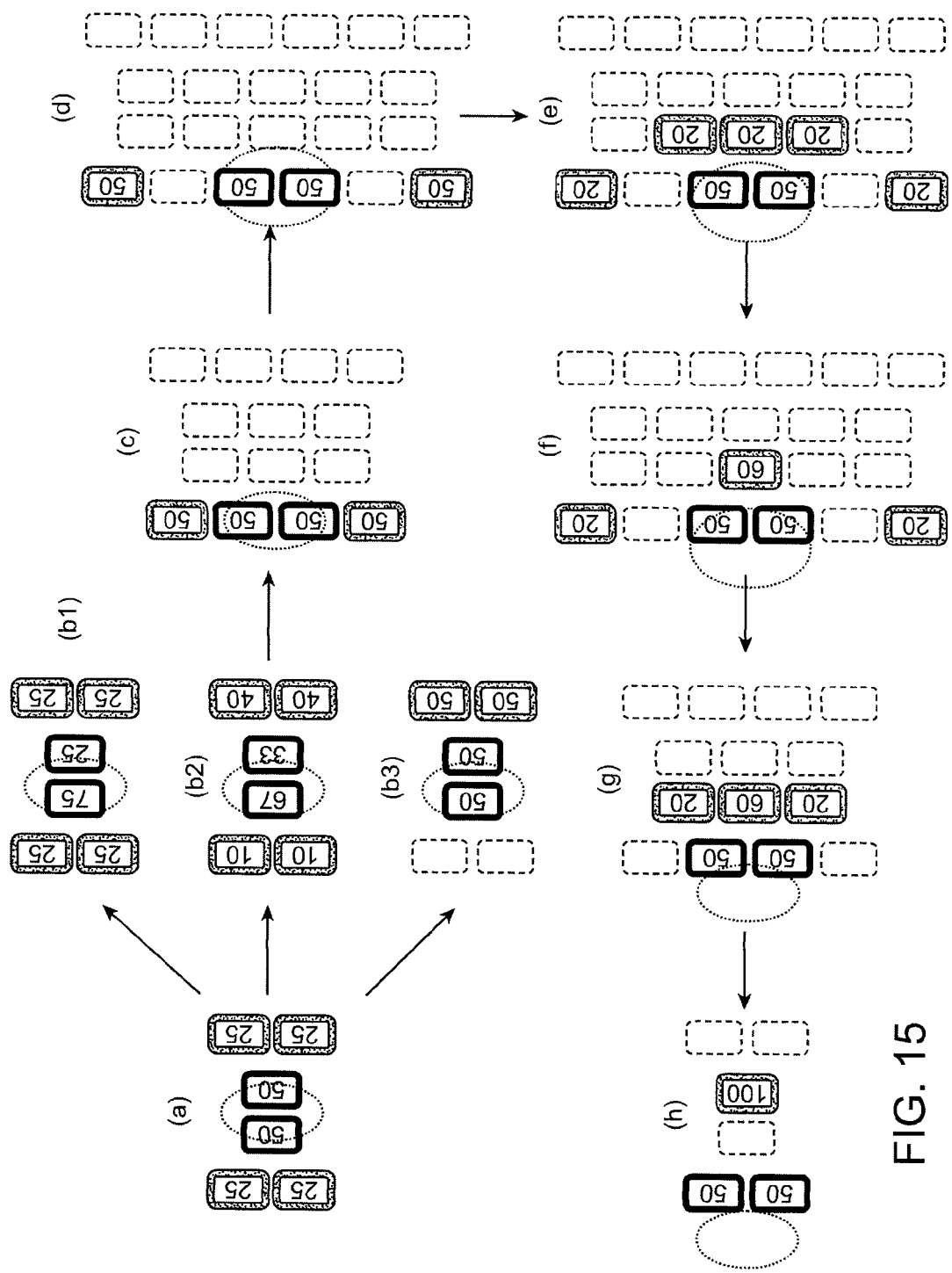
FIG. 15 is a coronal view of different electrode arrangements that can be used to gradually shifting the locus of a stimulation region from a medial position to a left lateral position.

With reference to FIG. 15, a technique for gradually shifting the locus of a stimulation region from a medial position to a left lateral position (i.e., from right to left) will now be described. In each electrode configuration, electrodes activated as cathodes are shown with dark solid black lines, electrodes activated as anodes are shown with grey solid lines, and non-activated electrodes are shown with dashed lines. The stimulation region generated by each electrode configuration is shown as an oval with dotted lines. This technique is especially useful when the paddle lead has migrated, and in this case, migrated from a medial position to a right lateral position, in which case, the locus of the stimulation region must be shifted back to the left relative to the paddle lead to maintain the same therapeutic effect.

Notably, when stimulating DC fibers, it is desirable that the ratio of the dorsal root (DR) threshold over the dorsal column (DC) threshold be as high as possible in order to minimize stimulation of the DR fibers. However, when shifting the stimulation region from a medial position to a lateral position, the DR/DC ratio will inevitably decrease. To minimize this adverse effect, it is preferably that the DR/DC ratio be decreased as smoothly and as little as possible. In making this transition as smoothly as possible, this technique combines rostro-caudal current steering using a longitudinal tripole (i.e., two anodes or anode groups with a cathode or cathode group) and quadrapole (i.e., three anodes or anode groups with a cathode or cathode group) with medio-lateral current steering.

For example, in the initial electrode configuration (a), two adjacent electrodes in the inner electrode columns are configured as cathodes, with each cathode having a fractionalized current of 50%, and two electrodes in each of the outer electrode columns are configured as anodes with each anode having a fractionalized current of 25%. This electrode configuration generates a medial-lateral electrical field that creates a stimulation region having its locus at the midline of the cathodes.

Next, the electrical current can be medio-laterally steered to one of the electrode configurations (b1), (b2), or (b3) to gradually displace the locus of the stimulation region to the left.

In electrode configuration (b1), two adjacent electrodes in the inner electrode columns are configured as cathodes, with the left cathode having a fractionalized current of 75% and the right cathode having a fractionalized current of 25%, and two electrodes in each of the outer electrode columns are configured as anodes with each anode having a fractionalized current of 25%. This electrode configuration displaces the locus of the stimulation region to the left of the midline of the cathodes via cathode steering.

In electrode configuration (b2), two adjacent electrodes in the inner electrode columns are configured as cathodes, with the left cathode having a fractionalized current of 67% and the right cathode having a fractionalized current of 33%, and two electrodes in each of the outer electrode columns are configured as anodes, with each of the left two anodes having a fractionalized current of 10%, and each of the right two anodes having a fractionalized current of 40%. This electrode configuration displaces the locus of the stimulation region to the left of the midline of the cathodes via cathode/anode steering.

In electrode configuration (b3), two adjacent electrodes in the inner electrode columns are configured as cathodes, with each of the cathodes having a fractionalized current of 50%, and two electrodes in only the right outer electrode columns are configured as anodes, with each of the right two anodes having a fractionalized current of 50%. This electrode configuration displaces the locus of the stimulation region to the left of the midline of the cathodes via anode steering.

Next, the electrical field can be medio-laterally steered from one of the electrode configurations (b1), (b2), or (b3) to electrode configuration (c) to gradually displace the locus of the electrical field to the left. In electrode configuration (c), two adjacent electrodes in the left outer electrode columns are configured as cathodes, and two electrodes in the left outer electrode columns immediately rostro-caudally flanking the cathodes are configured as anodes. This electrode configuration generates a rostro-caudal electrical field that creates a stimulation region having its locus centered on the left electrode column between the cathodes.

Next, the rostro-caudal electrical field is gradually broadened by shifting the cathodic current from electrode configuration (c) to electrode configuration (d), wherein the anodes are moved further out in the rostral/caudal direction. This will smooth out the transition to the next medio-lateral electrode configuration.

Then, electrode configuration (d) is gradually changed to electrode configuration (e), wherein the two adjacent electrodes in the left column remain cathodes that have a fractionalized current of 50% each, and some of the current has been shifted from the two anodes in the left column to three anodes in the left inner column adjacent the cathodes, so that each of the anodes has a fractionalized current of 20%. This electrode configuration results in a medio-lateral electrical field that displaces the locus of the stimulation region slightly to the left of the cathodes.

Next, electrode configuration (e) is gradually changed to electrode configuration (f) by shifting current in the two anodes rostro-caudally flanking the center anode in the left inner column to the center electrode, wherein the two adjacent electrodes in the left column remain cathodes that have a fractionalized current of 50% each, and all of the current in the flanking anodes in the left inner column has been shifted to the center anode, so that the anodes in the left outer column each has a fractionalized current of 20%, and the cathode in the left inner column has a fractionalized current of 60%. This electrode configuration results in a medio-lateral electrical field that further displaces the locus of the stimulation region to the left of the cathodes.

Next, electrode configuration (f) is gradually changed to electrode configuration (g) by shifting the current from the two anodes in the left outer column to the electrodes in the left inner column that rostro-caudally flank the center anode, wherein the two adjacent electrodes in the left column remain cathodes that have a fractionalized current of 50% each, and all of the current in the flanking anodes in the left outer column has been shifted to the flanking anodes in the left inner column, so that the flanking anodes in the left outer column each has a fractionalized current of 20%, and the cathode in the left inner column has a fractionalized current of 60%. This electrode configuration results in a medio-lateral electrical field that narrows the stimulation region and further displaces its locus to the left of the cathodes.

Lastly, electrode configuration (g) is gradually changed to electrode configuration (h) by shifting the current from the three anodes in the left inner column to the center electrode in the right inner column, wherein the two adjacent electrodes in the left column remain cathodes having a fractionalized current of 50% each, and the anode in the right inner column has a fractionalized current of 100%. This electrode configuration results in a medio-lateral electrical field that displaces the locus of the stimulation region even further to the left of the cathodes.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient, comprising:
    (a) disposing at least four electrodes adjacent spinal cord tissue of the patient in a medial-lateral electrode arrangement, wherein the at least four electrodes has two inner electrodes and two outer electrodes flanking the two inner electrodes;
    (b) conveying electrical energy between the electrodes to create a medial-lateral electrical field;
    (c) discretely moving a locus of the medial-lateral electrical field to one lateral side of the midline of the spinal cord tissue;
    (d) discretely moving the locus of the medial lateral electrical field to the other lateral side of the midline of the spinal cord tissue; and
    (e) repeating steps (c) and (d) to repeatedly move the locus of the medial-lateral field back and forth between the one lateral side and the other lateral side of the midline of the spinal cord tissue, whereby dorsal column nerve fibers on both sides of the midline of the spinal cord tissue are stimulated without stimulating the dorsal column nerve fibers along the midline of the spinal cord tissue.

2. The method of claim 1, wherein moving the locus of the medial-lateral electrical field to the one lateral side of the midline of the spinal cord tissue is accomplished by configuring only a first one of the inner electrodes as a cathode and configuring at least one of the outer electrodes as an anode, and wherein moving the locus of the medial-lateral electrical field to the other lateral side of the midline of the spinal cord tissue is accomplished by configuring only a second one of the inner electrodes as a cathode, and at least one of the outer electrodes as an anode.

3. The method of claim 1, wherein moving the locus of the medial-lateral electrical field to the one lateral side of the midline of the spinal cord tissue is accomplished by configuring a first one of the inner electrodes to have more cathodic current than a second one of the inner electrodes, and configuring at least one of the outer electrodes as an anode, and wherein moving the locus of the medial-lateral electrical field to the other lateral side of the midline of the spinal cord tissue is accomplished by configuring the second one of the inner electrodes to have more cathodic current than the first one of the inner electrodes, and configuring at least one of the outer electrodes as an anode.

4. The method of claim 1, wherein the medial-lateral electrical field stimulate the dorsal column fibers without stimulating dorsal root fibers within the spinal cord tissue.

5. The method of claim 1, wherein the at least four electrodes are disposed within the epidural space of a patient.

6. The method of claim 1, wherein the electrical energy is conveyed in a first timing channel to move the locus of the medial-lateral electrical field to the one lateral side of the midline of the spinal cord tissue, and the electrical energy is conveyed in a second timing channel to move the locus of the medial-lateral electrical field to the other lateral side of the midline of the spinal cord tissue.

7. A method of providing therapy to a patient using at least four electrodes disposed adjacent spinal cord tissue of the patient in a medial-lateral electrode arrangement, wherein the at least four electrodes has two inner electrodes and two outer electrodes flanking the two inner electrodes, the method comprising:
    (a) conveying electrical energy between the electrodes to create a medial-lateral electrical field, wherein at least one of the inner electrodes is configured as a cathode, and at least one of the outer electrodes is configured as an anode;
    (b) discretely moving a locus of the medial-lateral electrical field to one lateral side of the midline of the spinal cord tissue;
    (c) discretely moving the locus of the medial lateral electrical field to the other lateral side of the midline of the spinal cord tissue; and
    (d) repeating steps (b) and (c) to repeatedly move the locus of the medial-lateral field back and forth between the one lateral side and the other lateral side of the midline of the spinal cord tissue, whereby dorsal column nerve fibers on both sides of the midline of the spinal cord tissue are stimulated without stimulating the dorsal column nerve fibers along the midline of the spinal cord tissue.

8. The method of claim 7, wherein moving the locus of the medial-lateral electrical field to the one lateral side of the midline of the spinal cord tissue is accomplished by configuring only a first one of the inner electrodes as a cathode and configuring at least one of the outer electrodes as an anode, and wherein moving the locus of the medial-lateral electrical field to the other lateral side of the midline of the spinal cord tissue is accomplished by configuring only a second one of the inner electrodes as a cathode, and at least one of the outer electrodes as an anode.

9. The method of claim 7, wherein moving the locus of the medial-lateral electrical field to the one lateral side of the midline of the spinal cord tissue is accomplished by configuring a first one of the inner electrodes to have more cathodic current than a second one of the inner electrodes, and configuring at least one of the outer electrodes as an anode, and wherein moving the locus of the medial-lateral electrical field to the other lateral side of the midline of the spinal cord tissue is accomplished by configuring the second one of the inner electrodes to have more cathodic current than the first one of the inner electrodes, and configuring at least one of the outer electrodes as an anode.

10. The method of claim 7, wherein the medial-lateral electrical field stimulate the dorsal column fibers without stimulating dorsal root fibers within the spinal cord tissue.

11. The method of claim 7, wherein the at least four electrodes are disposed within the epidural space of a patient.

12. The method of claim 7, wherein the electrical energy is conveyed in a first timing channel to move the locus of the medial-lateral electrical field to the one lateral side of the midline of the spinal cord tissue, and the electrical energy is conveyed in a second timing channel to move the locus of the medial-lateral electrical field to the other lateral side of the midline of the spinal cord tissue.

* * * * *